US006214580B1

(12) United States Patent
Ni et al.

(10) Patent No.: US 6,214,580 B1
(45) Date of Patent: *Apr. 10, 2001

(54) HUMAN TUMOR NECROSIS FACTOR RECEPTOR TR10

(75) Inventors: Jian Ni, Rockville; Craig A. Rosen, Laytonsville, both of MD (US)

(73) Assignee: Human Genome Sciences, Inc., Rockville, MD (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/086,483

(22) Filed: May 29, 1998

Related U.S. Application Data

(60) Provisional application No. 60/050,936, filed on May 30, 1997, and provisional application No. 60/069,112, filed on Dec. 9, 1997.

(51) Int. Cl.[7] ..................................................... C12N 15/12
(52) U.S. Cl. ................... 435/69.1; 536/23.5; 435/320.1; 435/252.3; 435/325
(58) Field of Search ........................ 536/23.5; 435/320.1, 435/252.3, 69.1; 530/388.22; 514/2

(56) References Cited

U.S. PATENT DOCUMENTS 5,705,379 * 1/1998 Wilson et al. ....................... 435/220

FOREIGN PATENT DOCUMENTS

| WO 99/03992 | 1/1999 | (WO) . |
| WO 99/07850 | 2/1999 | (WO) . |
| WO 99/10484 | 3/1999 | (WO) . |

OTHER PUBLICATIONS

Hillier et al, The WashU–Merck EST Project, accession number T66968, Homo sapiens Soares fetal liver spleen cDNA clone 66516, Mar. 7, 1995.*
Hillier et al, The WashU–Merck EST Project, accession number T71406, Homo sapiens Soares fetal liver spleen cDNA clone 110226, Mar. 15, 1995.*
Hillier et al, The WashU–Merck EST Project, accession number AA150849, Homo sapiens Soares pregnant uterus NbHPU cDNA clone 504745, May 19, 1997.*
Walczak et al., The EMBO Journal, 16(17):5386–5397 (1997).
Marsters et al., Current Biology, 7(12):1003–1006 (1997).
Pan et al., FEBS Letters, 424:41–45 (1998).
Marsters et al. (1997) Current Biology vol. 7 (12):1003–1006.
Degli–Esposti et al. (1997) Immunity 7:813–820.
Pan et al. (1998) FEBS Lett.424:41–45.
Genbank Accession No. B32806 (Oct. 17, 1997).
Genbank Accession No. AA568830 (Aug. 22, 1997).
Genbank Accession No. AA705297 (Dec. 24, 1997).
Genbank Accession No. H71883 (Oct. 26, 1995).
Genbank Accession No. T66968 (Mar. 7, 1995).
Genbank Accession No. AA374242 (Apr. 21, 1997).
Genbank Accession No. R16589 (Apr. 14, 1995).
Genbank Accession No. W52137 (Oct. 11, 1996).
Genbank Accession No. AA345927 (Apr. 21, 1997).
Genbank Accession No. R00173 (Mar. 31, 1995).
Genbank Accession No. R16532 (Apr. 14, 1995).
Genbank Accession No. T66967 (Mar. 7, 1995).
Genbank Accession No. H71094 (Oct. 26, 1995).
Genbank Accession No. AA150849 (May 19, 1997).
Genbank Accession No. T71406 (Mar. 15, 1995).

* cited by examiner

Primary Examiner—Lorraine Spector
Assistant Examiner—Eileen B. O'Hara
(74) Attorney, Agent, or Firm—Human Genome Sciences, Inc

(57) ABSTRACT

The present invention relates to a novel protein, TR10, which is a member of the tumor necrosis factor (TNF) receptor superfamily and the TRAIL receptor subfamily. In particular, isolated nucleic acid molecules are provided encoding the human TR10 protein. TR10 polypeptides are also provided as are vectors, host cells and recombinant methods for producing the same. The invention further relates to screening methods for identifying agonists and antagonists of TR10 activity.

109 Claims, 10 Drawing Sheets

CGACCCACGGCGTCCGCCCACGCGTCCGGAGAACCTTTGCACGGCGCACAAACTACGGGGAC

GATTTCTGATTGATTTTTGGGCGCTTTCGATCCACCCCTCCCCTTCTCATGGGACTTTGG
                                                    M  G  L  W

GGACAAAGCGTCCCGACCGCCTCGAGCAGGGCGCTATCCAGGAGCCAGGACA
 G  Q  S  V  P  T  A  S  S  A  R  A  G  R  Y  P  G  A  R  T

GCGTCGGGGAACCAGAGACCATGGCTCCTGGACCCCCAAGATCCTTAAGTTCGTCTTCATC
 A  S  G  T  R  P  W  L  L  D  P  K  I  L  K  F  V  F  I

GTCGCGGGTTCTGCTGCCGGTCCGGTTGACTCTGCCACCATCCCCGGCAGGACGAAGTT
 V  A  V  L  P  V  R  V  D  S  A  T  I  P  R  Q  D  E  V

CCCCAGCAGACAGTGGCCCCACAGCAACAGAGGCGCAGCCTCAAGGAGGAGTGTCCA
 P  Q  Q  T  V  A  P  Q  Q  R  R  S  L  K  E  E  C  P

GCAGGATCTCATAGATCAGAATATACTGGAGCCTGTAACCCGTGCACAGAGGGTGTGGAT
 A  G  S  H  R  S  E  Y  T  G  A  C  N  P  C  T  E  G  V  D

TACACCATTGCTTCCAACAATTGCCTTCTTGCCTGCTATGTACAGTTTGTAAATCAGGT
 Y  T  I  A  S  N  N  L  P  S  C  L  C  T  V  C  K  S  G

FIG. 1A

```
                          490                        510                                 530
CAAACAAATAAAAGTTCCTGTACCACGAGACCAGAGACACCGTGTGTCAGTGTGAAAAAGGA
 Q  T  N  K  S  S  C  T  T  T  R  D  T  V  C  Q  C  E  K  G
                    550                        570                             590
AGCTTCCAGGATAAAAACTCCCCTGAGATGTGCCGGACGTGTAGAACAGGGTGTCCCAGA
 S  F  Q  D  K  N  S  P  E  M  C  R  T  C  R  T  G  C  P  R
              610                        630                             650
GGGATGGTCAAGGTCAGTAATTGTACGCCCGGAGTGACATCAAGTGCAAAAATGAATCA
 G  M  V  K  V  S  N  C  T  P  R  S  D  I  K  C  K  N  E  S
        670                        690                             710
GCTGCCAGTTCCACTGGGAAAACCCCAGCAGCAGAGGAGACAGTGACCACCATCCTGGGG
 A  A  S  S  T  G  K  T  P  A  A  E  E  T  V  T  T  I  L  G
                    730                        750                             770
ATGCTTGCCTCTCCCTATCACTACCTTATCATCATAGTGGTTTTTAGTCATCATTTTAGCT
 M  L  A  S  P  Y  H  Y  L  I  I  I  V  V  L  V  I  I  L  A
              790                        810                             830
GTGGTTGTGGTTGGCTTTTTCATGTCGGAAGAAATTCATTTCTTACCTCAAAGGCATCTGC
 V  V  V  G  F  S  C  R  K  K  F  I  S  Y  L  K  G  I  C
        850                        870                             890
TCAGGTGGTGGAGGAGGTCCCGAACGTGTGCACAGAGTCCTTTTCCGGCGGTTCATGT
 S  G  G  G  G  G  P  E  R  V  H  R  V  L  F  R  R  S  C
                    910                        930                             950
CCTTCACGAGTTCCTGGGGCGGAGGACAATGCCCGCAACGAGACCCTGAGTAACAGATAC
 P  S  R  V  P  G  A  E  D  N  A  R  N  E  T  L  S  N  R  Y
```

FIG. 1B

```
                                970                          990                                1010
TTGCAGCCCACCCAGGTCTCTGAGCAGGAGAAATCCAAGGTCAGGAGAGCTGGCAGAGCTAACA
 L  Q  P  T  Q  V  S  E  Q  E  I  Q  G  Q  E  L  A  E  L  T
                  1030                          1050                          1070
GGTGTGACTGTAGAGTCGCCAGAGGAGCCACAGCGTCTGCTGGAACAGGCAGAAGCTGAA
 G  V  T  V  E  S  P  E  E  P  Q  R  L  L  E  Q  A  E  A  E
                  1090                          1110                          1130
GGGTGTGTCAGAGGAGGCTGCTGGTTCCAGTGAATGACGCTGACTCCGCTGACATCAGC
 G  C  Q  R  R  L  L  V  P  V  N  D  A  D  S  A  D  I  S
                  1150                          1170                          1190
ACCTTGCTGGATGCCTCGGCCAACACTCTGGAAGGACATGCAAAGGAAACAATTCAGGAC
 T  L  L  D  A  S  A  T  L  E  G  H  A  K  E  T  I  Q  D
                  1210                          1230                          1250
CAACTGGTGGGCTCCGAAAAGCTCTTTTATGAAGAAGATGAGGCAGGCAGCGCTGCTACGTCC
 Q  L  V  G  S  E  K  L  F  Y  E  E  D  E  A  G  S  A  T  S
                  1270                          1290                          1310
TGCCCTGTGAAAGAATCTCTTCAGGAAACCAGAGCTTCCCTCATTTACCTTTCTCCTACA
 C  L  *
                  1330                          1350                          1370
AAGGGAAGCAGCCTGGAAGAAACAGTCCAGTACTTGACCCATGCCCCAACAAACTCTACT
                  1390                          1410                          1430
ATCCAATATGGGCAGCTTACCAATGTCCTAGAACTTTGTTAACGCACTTGGAGTAATT
                  1450                          1470                          1490
TTTATGAAATACTGCGTGTGATAAGCAAACGGGAGAAATTTATATCAGATTCTTGGCTGC
```

FIG. 1C

```
                                                                   1530                            1550
ATAGTTATACGATTGTGTATTAAGGGTCGTTTTAGGCCACATGCGGTGGCTCATGCCTGT
            1570                            1590                            1610
AATCCCAGCACTTTGATAGGCTGAGGCAGGTGGATTGCTTTGAGCTCGGGAGTTTGAGAC
            1630                            1650                            1670
CAGCCTCATCAACACAGTGAAACTCCATCTCAATTTAAAAAGAAAAAAGTGGTTTTAG
            1690                            1710                            1730
GATGTCATTCTTTGCAGTTCTTCATCATGAGACAAGTCTTTTTTTCTGCTTCTTATATTG
            1750                            1770                            1790
CAAGCTCCATCTCTACTGGTGTGCATTAATGACATCTAACTACAGATGCCGCACAGC
            1810                            1830                            1850
CACAATGCTTTGCCTTATAGTTTTTTAACTTTAGAACGGGATTATCTTGTTATTACCTGT
            1870                            1890                            1910
ATTTTCAGTTTCGGATATTTTTGACTTAATGATGAGATTATCAAGACGTAGCCCTATGCT
            1930                            1950                            1970
AAGTCATGAGCATATGGACTTACGAGGGTTCGACTTAGAGTTTTGAGCTTTAAGATAGGA
            1990                            2010                            2030
TTATTGGGCTTACCCCCCACCTTAATTAGAGAAACATTTATATTGCTTACTACTGTAGGC
            2050                            2070                            2090
TGTACATCTCTTTTCCGATTTTTGTATAATGATGTAAACATGGAAAAACTTTAGGAAATG
            2110                            2130                            2150
CACTTATTAGGCTGTGTTTACATGGGTTGCCTGGATACAAATCAGCAGTCAAAAATGACTAA
            2170                            2190                            2210
AAATATAACTAGTGACGGAGGGAGAAATCCCTCTGTGGGAGGCACTTACTGCATTCC
```

FIG. 1D

```
                                                                2250                                    2270
AGTTCTCCCTCCTGCGCCCTGAGACTGGACCAGGGTTTGATGGCTGGCAGCTTCTCAAGG
        2290                                    2310                                    2330
GGCAGCTTGTCTTACTTGTGTTAATTTTAGAGGTATATAGCCATATATTTATTATAAATAAAT
                2350                                    2370                                    2390
ATTTATTTATTTATTTATAAGTAGATGTTTACATATGCCCAGGATTTGAAGAGCCTGGT
                        2410                                    2430                                    2450
ATCTTTGGGAAGCCATGTGTCTGGTTTGTCGTGCTGGGACAGTCATGGGACTGCATCTTC
                                2470                                    2490                                    2510
CGACTTGTCCACAGCAGATGAGGACAGTGAGAATTAAGTTAGATCCGAGACTGCGAAGAG
                                        2530                                    2550                                    2570
CTTCTCTTTCAAGCGCCATTACAGTTGAACGTTAGTGAATCTTGAGCCTCATTTGGGCTC
                                                2590                                    2610                                    2630
AGGGCAGAGCAGGTGTTTATCTGCCCCGGCATCTGCCATGGCATCAAGAGGGAAGAGTGG
                                                        2650                                    2670                                    2690
ACGGTGCTTGGGACTGTGTGAAATGGTTGCCGACTCAGGCATGGGCCCCTCTCGC
                                                                2710                                    2730                                    2750
TTCTGGTGGTCTGTGAACTGAGTCCCTGGGATGCCTTTTAGGGCAGAGATTCCTGAGCTG
                                                                        2770                                    2790                                    2810
CGTTTTAGGGTACAGATTCCCTGTTTGAGGAGCTTGGCCCCTCTGTAAGCATCTGACTCA
                                                                                2830                                    2850                                    2870
TCTCAGAGATATCAATTCTTAAACACTGTGACAACGGGATCTAAAAATGGCTGACACATTT
                                                                                        2890                                    2910                                    2930
GTCCTTGTGTCACGTTCCATTATTTTATTTAAAAACCTCAGTAATCGTTTTAGCTTTCTTT
```

FIG. 1E

```
                                                                    2970                      2990
CCAGCAAACTCTTCTCCACAGTAGCCCAGTAGCCCAGTCGTGGTAGGATAAATTACGGATATAGTCAT
         3010                           3030                          3050
TCTAGGGGTTTCAGTCTTTTCCATCTCAAGGCATTGTGTTTGTTCCGGGACTGGTTT
         3070                           3090                          3110
GGCTGGGACAAAGTTAGAACTGCCTGAAGTTCGCACATTCAGATTGTTGTCCATGGAG
         3130                           3150                          3170
TTTTAGGAGGGGATGGCCCTTTCCGGTCTTCGCACTTCCATCCCTCCCCACTTCCCATCT
         3190                           3210                          3230
GGCGTCCCACACCTTGTCCCCCTGCCACTTCTGGATGACCAGGGTGCTGCCTCCTAGT
         3250                           3270                          3290
CTTTGCCTTTGCTGGGCCTTCTGTGCAGGAGACTTGGTCTCAAAGCTCAGAGAGCCAG
         3310                           3330                          3350
TCCGGTCCCAGCTCCCTTGTCCCTCAGAGGCCCTTCCTTGAAGATGCATCTAGACTA
         3370                           3390                          3410
CCAGCCTTATCAGTGTTTAAGCTTATTCCTTTAACATAAGCTTCCTGACAACATGAAATT
         3430                           3450                          3470
GTTGGGGTTTTTGGCGTTTGTTGATTGTTTAGGTTTTGCTTTATACCCGGGCCAAATA
         3490                           3510                          3530
GCACATAACACCTGGTTATATATGAAATACTCATATGTTTATGACCAAAATAAATATGAA
         3550
ACCTCAAAAAAAAAAAAAAAAA
```

HUMAN TUMOR NECROSIS FACTOR RECEPTOR TR10

PRIORITY

This application claims benefit of 35 U.S.C. section 119(e) based on copending U.S. Provisional Application Ser. Nos. 60/050,936, filed May 30, 1997, and 60/069,112, filed Dec. 9, 1997, both of which are herein incorporated by reference in their entirety.

BACKGROUND OF THE INVENTION

1. Field of the Invention

The present invention relates to a novel member of the tumor necrosis factor family of receptors. More specifically, isolated nucleic acid molecules are provided encoding a novel human tumor necrosis factor receptor, TR10. TR10 polypeptides are also provided, as are vectors, host cells, and recombinant methods for producing the same. The invention further relates to screening methods for identifying agonists and antagonists of TR10 activity.

2. Related Art

Many biological actions, for instance, response to certain stimuli and natural biological processes, are controlled by factors, such as cytokines. Many cytokines act through receptors by engaging the receptor and producing an intracellular response.

For example, tumor necrosis factors (TNF) alpha and beta are cytokines, which act through TNF receptors to regulate numerous biological processes, including protection against infection and induction of shock and inflammatory disease. The TNF molecules belong to the "TNF-ligand" superfamily, and act together with their receptors or counter-ligands, the "TNF-receptor" superfamily. So far, nine members of the TNF ligand superfamily have been identified and ten members of the TNF-receptor superfamily have been characterized.

Among the ligands there are included TNF-α, lymphotoxin-α (LT-α, also known as TNF-β), LT-β (found in complex heterotrimer LT-α2-β), FasL, CD40L, CD27L, CD30L, 4-1BBL, OX40L and nerve growth factor (NGF). The superfamily of TNF receptors includes the p55TNF receptor, p75TNF receptor, TNF receptor-related protein, FAS antigen or APO-1, CD40, CD27, CD30, 4-1BB, OX40, low affinity p75 and NGF-receptor (A. Meager, *Biologicals* 22:291–295 (1994)).

Many members of the TNF-ligand superfamily are expressed by activated T-cells, implying that they are necessary for T-cell interactions with other cell types which underlie cell ontogeny and functions. (A. Meager, supra).

Considerable insight into the essential functions of several members of the TNF receptor family has been gained from the identification and creation of mutants that abolish the expression of these proteins. For example, naturally occurring mutations in the FAS antigen and its ligand cause lymphoproliferative disease (R. Watanabe-Fukunaga et al., *Nature* 356:314 (1992)), perhaps reflecting a failure of programmed cell death. Mutations of the CD40 ligand cause an X-linked immunodeficiency state characterized by high levels of immunoglobulin M and low levels of immunoglobulin G in plasma, indicating faulty T-cell-dependent B-cell activation (R. C. Allen et al, *Science* 259:990 (1993)). Targeted mutations of the low affinity nerve growth factor receptor cause a disorder characterized by faulty sensory innovation of peripheral structures (K. F. Lee et al., *Cell* 69:737 (1992)).

TNF and LT- are capable of binding to two TNF receptors (the 55- and 75-kd TNF receptors). A large number of biological effects elicited by TNF and LT-α, acting through their receptors, include hemorrhagic necrosis of transplanted tumors, cytotoxicity, a role in endotoxic shock, inflammation, immunoregulation, proliferation and antiviral responses, as well as protection against the deleterious effects of ionizing radiation. TNF and LT-α are involved in the pathogenesis of a wide range of diseases, including endotoxic shock, cerebral malaria, tumors, autoimmune disease, AIDS and graft-host rejection (B. Beutler and C. Von Huffel, *Science* 264:667–668 (1994)). Mutations in the p55 receptor cause increased susceptibility to microbial infection.

Moreover, an about 80 amino acid domain near the C-terminus of TNFR1 (p55) and Fas was reported as the "death domain," which is responsible for transducing signals for programmed cell death (Tartaglia et al., *Cell* 74:845 (1993)).

Apoptosis, or programmed cell death, is a physiologic process essential to the normal development and homeostasis of multicellular organisms (H. Steller, *Science* 267:1445–1449 (1995)). Derangements of apoptosis contribute to the pathogenesis of several human diseases including cancer, neurodegenerative disorders, and acquired immune deficiency syndrome (C. B. Thompson, *Science* 267:1456–1462 (1995)). Recently, much attention has focused on the signal transduction and biological function of two cell surface death receptors, Fas/APO-1 and TNFR-1 (J. L. Cleveland et al., *Cell* 81:479–482 (1995); A. Fraser et al., *Cell* 85:781–784 (1996); S. Nagata et al., *Science* 267:1449–56 (1995)). Both are members of the TNF receptor family, which also include TNFR-2, low affinity NGFR, CD40, and CD30, among others (C. A. Smith et al., *Science* 248: 1019–23 (1990); M. Tewari et al., in *Modular Texts in Molecular and Cell Biology* M. Purton, Heldin, Carl, Ed. (Chapman and Hall, London, 1995). While family members are defined by the presence of cysteine-rich repeats in their extracellular domains, Fas/APO-1 and TNFR-1 also share a region of intracellular homology, appropriately designated the "death domain," which is distantly related to the Drosophila suicide gene, reaper (P. Golstein et al., *Cell* 81:185–6 (1995); K. White et al., *Science* 264:677–83 (1994)). This shared death domain suggests that both receptors interact with a related set of signal transducing molecules that, until recently, remained unidentified. Activation of Fas/APO-1 recruits the death domain-containing adapter molecule FADD/MORT1 (A. M. Chinnaiyan et al., *Cell* 81:505–512 (1995); M. P. Boldin et al., *J. Biol. Chem.* 270:7795–8 (1995); F. C. Kischkel et al., *EMBO* 14:5579–5588 (1995)), which in turn binds and presumably activates FLICE/MACH1, a member of the ICE/CED-3 family of pro-apoptotic proteases (M. Muzio et al., *Cell* 85: 817–827 (1996); M. P. Boldin et al., *Cell* 85:803–815 (1996)). While the central role of Fas/APO-1 is to trigger cell death, TNFR-1 can signal an array of diverse biological activities-many of which stem from its ability to activate NF-kB (L. A. Tartaglia et al., *Immunol Today* 13:151–153 (1992)). Accordingly, TNFR-1 recruits the multivalent adapter molecule TRADD, which like FADD, also contains a death domain (H. Hsu et al., *Cell* 81:495–504 (1995); H. Hsu et al., *Cell* 84:299–308 (1996)). Through its associations with a number of signaling molecules including FADD, TRAF2, and RIP, TRADD can signal both apoptosis and NF-kB activation (H. Hsu et al., *Cell* 84:299–308 (1996); H. Hsu et al., *Immunity* 4:387–396 (1996)).

Recently, a new apoptosis inducing TNF ligand has been discovered. S. R. Wiley et al., *Immunity* 3:673–682 (1995), named the new molecule, "TNF-related apoptosis-inducing ligand" or "TRAIL." R. M. Pitti et al., *J. Biol. Chem.* 271:12687–12690 (1996), named the molecule "Apo-2 ligand" or "Apo-2L." This molecule was also disclosed in co-pending U.S. provisional patent application No. 60/013405. For convenience, this molecule will be referred to herein as TRAIL.

Unlike FAS ligand, whose transcripts appear to be largely restricted to stimulated T-cells, significant levels of TRAIL are detected in many human tissues (e.g., spleen, lung, prostate, thymus, ovary, small intestine, colon, peripheral blood lymphocytes, placenta, kidney), and it is constitutively transcribed by some cell lines. It has been shown that TRAIL acts independently from the FAS ligand (S. R. Wiley et al., supra). It has also been shown that TRAIL activates apoptosis rapidly, within a time frame that is similar to death signaling by Fas/Apo-1L, but much faster than TNF-induced apoptosis. S. A. Marsters et al., *Current Biology* 6:750–752 (1996). The inability of TRAIL to bind TNFR-1, Fas, or the recently identified DR3, suggests that TRAIL may interact with a unique receptor(s).

Work to date suggests that there are several unique TNF receptors for TRAIL. In co-pending U.S. provisional patent application No. 60/035,722, one novel death domain containing receptor for TRAIL, DR4, was disclosed. See, Pan et al., *Science* 276:111–113 (April 1997). In co-pending U.S. provisional patent application No. 60/040,846, a novel death domain containing receptor, DR5 (TR7), was disclosed. This receptor has now been shown to bind TRAIL. In co-pending U.S. provisional patent application No. 60/035,496, another receptor, TR5, was disclosed. This receptor has also now been shown to bind TRAIL, however, TR5 has been shown to be a non-signaling decoy receptor which antagonizes apoptosis.

The effects of TNF family ligands and receptors are varied and influence numerous functions, both normal and abnormal, in the biological processes of the mammalian system. There is a clear need, therefore, for identification and characterization of such receptors and ligands that influence biological activity, both normally and in disease states. In particular, there is a need to isolate and characterize additional novel receptors that bind TRAIL.

SUMMARY OF THE INVENTION

The present invention provides isolated nucleic acid molecules comprising a polynucleotide encoding the TR10 receptor having the amino acid sequence shown in SEQ ID NO:2 or the amino acid sequence encoded by the cDNA clone deposited as ATCC Deposit No. 209040 on May 15, 1997.

The present invention also relates to recombinant vectors, which include the isolated nucleic acid molecules of the present invention, and to host cells containing the recombinant vectors, as well as to methods of making such vectors and host cells and for using them for production of TR10 polypeptides or peptides by recombinant techniques.

The invention further provides an isolated TR10 polypeptide having an amino acid sequence encoded by a polynucleotide described herein.

The present invention also provides diagnostic assays such as quantitative and diagnostic assays for detecting levels of TR10 protein. Thus, for instance, a diagnostic assay in accordance with the invention for detecting overexpression of TR 10, or soluble form thereof, compared to normal control tissue samples may be used to detect the presence of tumors.

Tumor Necrosis Factor (TNF) family ligands are known to be among the most pleiotropic cytokines, inducing a large number of cellular responses, including cytotoxicity, antiviral activity, immunoregulatory activities, and the transcriptional regulation of several genes. Cellular response to TNF-family ligands include not only normal physiological responses, but also diseases associated with increased apoptosis or the inhibition of apoptosis. Apoptosis-programmed cell death-is a physiological mechanism involved in the deletion of peripheral T lymphocytes of the immune system, and its dysregulation can lead to a number of different pathogenic processes. Diseases associated with increased cell survival, or the inhibition of apoptosis, include cancers, autoimmune disorders, viral infections, inflammation, graft vs. host disease, acute graft rejection, and chronic graft rejection. Diseases associated with increased apoptosis include AIDS, neurodegenerative disorders, myelodysplastic syndromes, ischemic injury, toxin-induced liver disease, septic shock, cachexia, and anorexia.

Thus, the invention further provides a method for inhibiting apoptosis induced by a TNF-family ligand, which involves administering to a cell which expresses the TR10 polypeptide an effective amount of an agonist capable of increasing TR10 mediated signaling. Preferably, TR10 mediated signaling is increased to treat a disease wherein increased apoptosis is exhibited.

In a further aspect, the present invention is directed to a method for enhancing apoptosis induced by a TNF-family ligand, which involves administering to a cell which expresses the TR10 polypeptide an effective amount of an antagonist capable of decreasing TR10 mediated activity. Preferably, TR10 mediated activity is decreased to treat a disease wherein decreased apoptosis is exhibited.

Whether any candidate "agonist" or "antagonist" of the present invention can enhance or inhibit apoptosis can be determined using art-known TNF-family ligand/receptor cellular response assays, including those described in more detail below. Thus, in a further aspect, a screening method is provided for determining whether a candidate agonist or antagonist is capable of enhancing or inhibiting a cellular response to a TNF-family ligand. The method involves contacting cells which express the TR10 polypeptide with a candidate compound and a TNF-family ligand, assaying a cellular response, and comparing the cellular response to a standard cellular response, the standard being assayed when contact is made with the ligand in absence of the candidate compound, whereby an increased cellular response over the standard indicates that the candidate compound is an agonist of the ligand/receptor signaling pathway and a decreased cellular response compared to the standard indicates that the candidate compound is an antagonist of the ligand/receptor signaling pathway. By the invention, a cell expressing the TR10 polypeptide can be contacted with either an endogenous or exogenously administered TNF-family ligand.

BRIEF DESCRIPTION OF THE FIGURES

FIGS. 1A–F shows the nucleotide (SEQ ID NO:1) and deduced amino acid sequence (SEQ ID NO:2) of the TR10 receptor. Predicted amino acids 1–55 constitute the signal peptide (amino acid residues from about –55 to about –1 in SEQ ID NO:2); amino acids 56–212 constitute the extracellular domain (amino acid residues from about 1 to about 157 in SEQ ID NO:2); amino acids 213–230 constitute the transmembrane domain (amino acid residues from about 158 to about 175 in SEQ ID NO:2); and amino acids 231–386 constitute the intracellular domain (amino acid residues from about 176 to about 331 in SEQ ID NO:2), of which amino acids 353–363 constitute the partial death domain (amino acid residues from about 298 to about 308 in SEQ ID NO:2).

FIGS. 2A–B shows the regions of similarity between the amino acid sequences of the TR10 receptor protein (SEQ ID NO:2), and the Fas receptor (SEQ ID NO:3), NGFR p75 (SEQ ID NO:4), human TNFR 1 (SEQ ID NO:5), and DR4 (SEQ ID NO:6).

DETAILED DESCRIPTION OF THE PREFERRED EMBODIMENTS

Figure 2B:
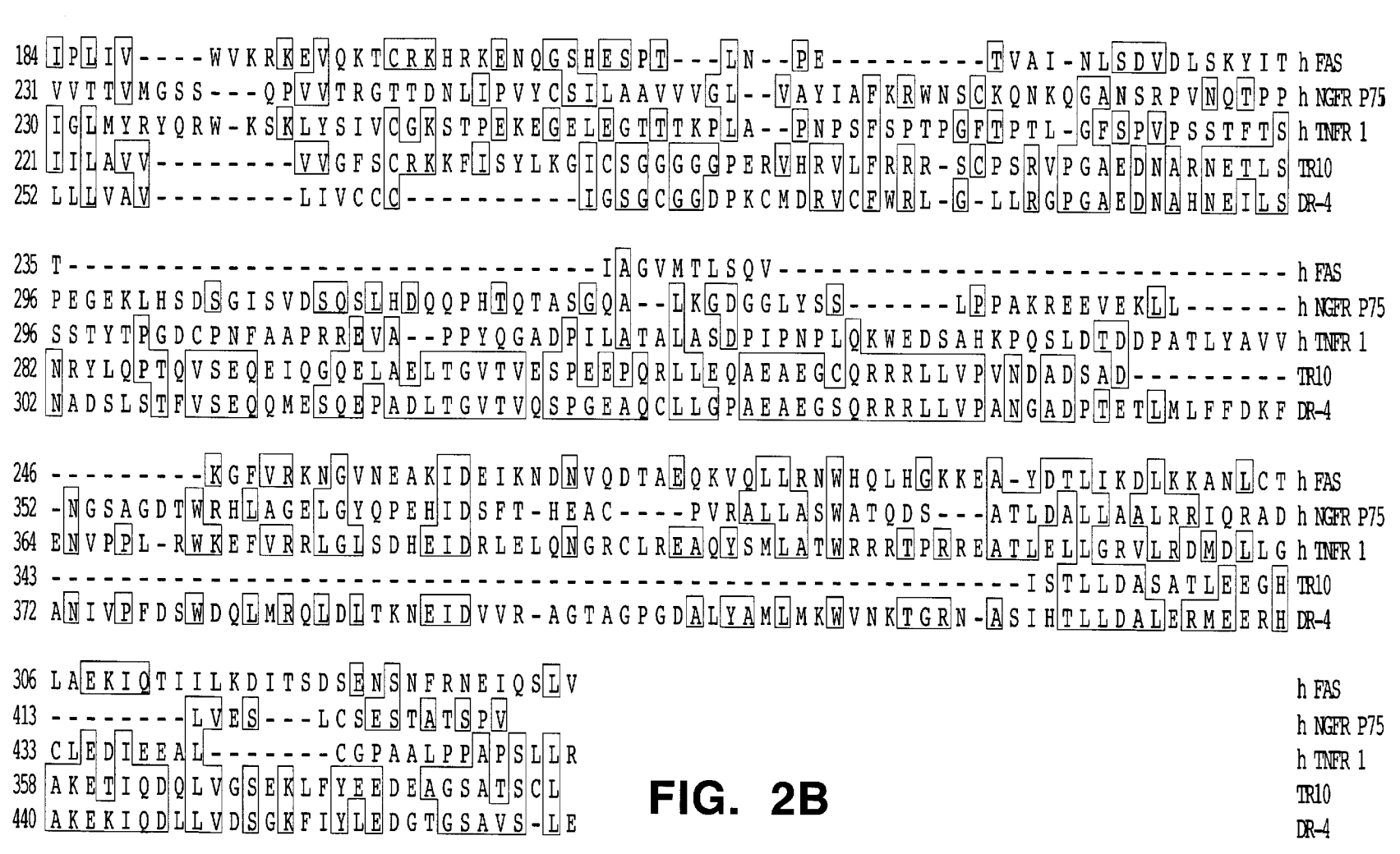
Figure 3A:
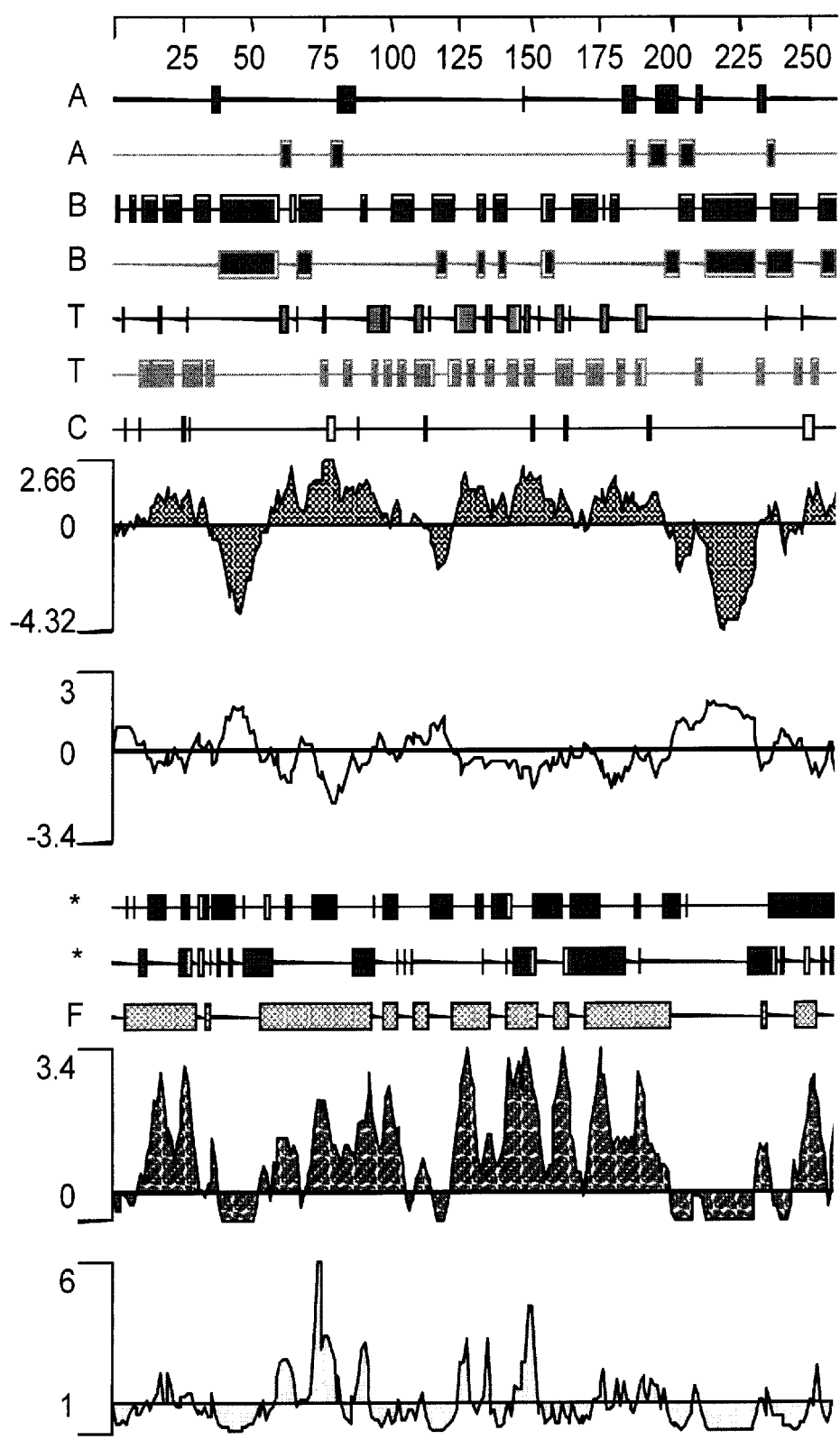
FIGS. 3A–B shows an analysis of the TR10 amino acid sequence. Alpha, beta, turn and coil regions; hydrophilicity and hydrophobicity; amphipathic regions; flexible regions; antigenic index and surface probability are shown. In the "Antigenic Index—Jameson-Wolf" graph, amino acid residues about 57 to about 113, about 130 to about 197, and about 250 to about 283 in FIGS. 1A–F correspond to the shown highly antigenic regions of the TR10 protein. These highly antigenic fragments in FIGS. 1A–F correspond to the following fragments, respectively, in SEQ ID NO:2: amino acid residues from about 2 to about 58, from about 75 to about 142, and from about 195 to about 228.
Figure 3B:
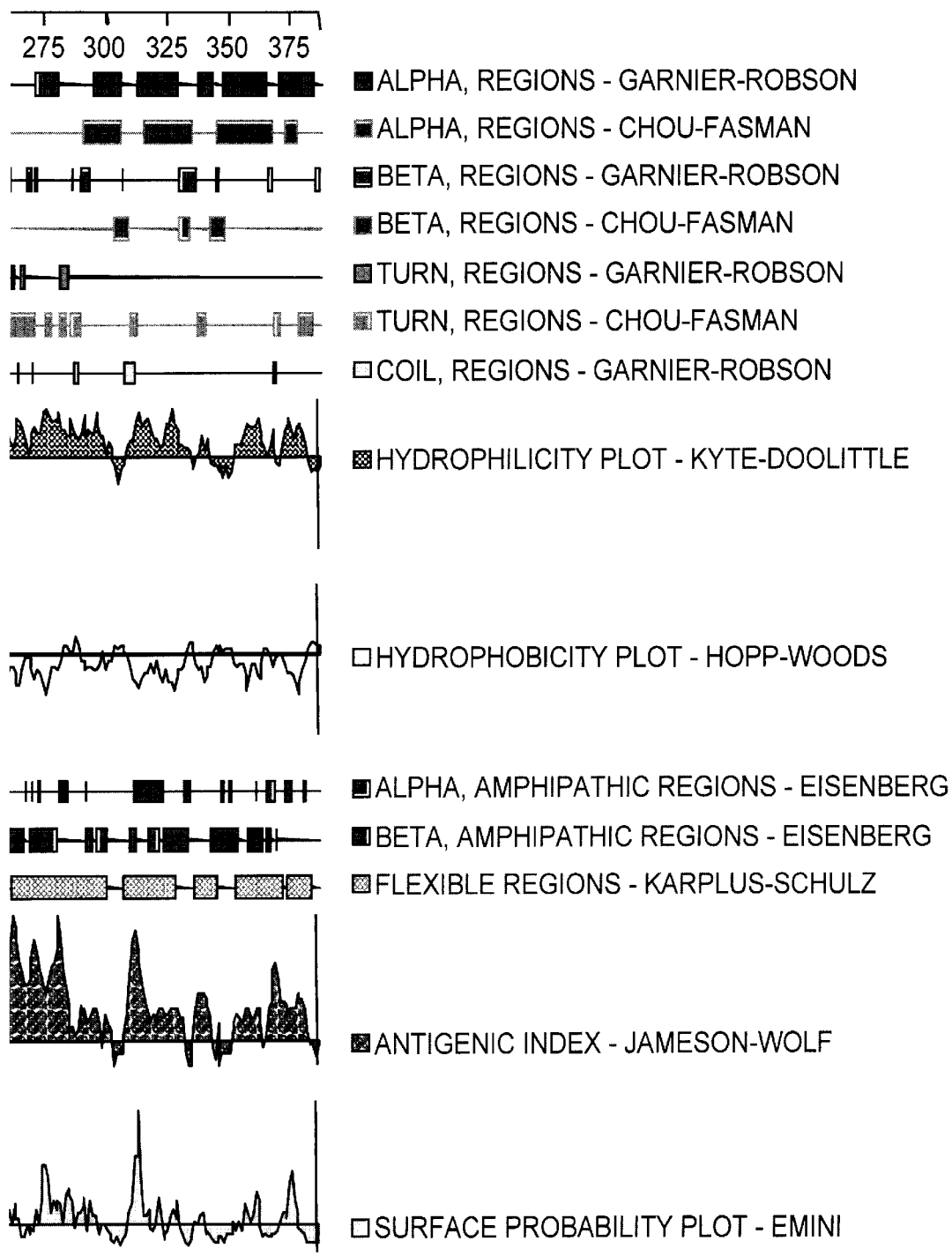

The present invention provides isolated nucleic acid molecules comprising a polynucleotide encoding a TR10 polypeptide having the amino acid sequence shown in FIGS. 1A–F (SEQ ID NO:2), which was determined by sequencing a cloned cDNA. The TR10 polypeptide of the present invention shares sequence homology with human NGFR, TNFRI, DR4, and Fas (FIGS. 2A–B). The nucleotide sequence shown in FIGS. 1A–F (SEQ ID NO:1) was obtained by sequencing a cDNA clone, which was deposited on May 15, 1997 at the American Type Culture Collection, 10801 University Boulevard, Manassas, Va. 20110-2209 and given Accession Number 209040. The deposited clone is inserted in the pCMVSport 2.0 plasmid (Life Technologies, Rockville, Md.) sing the Sal I/Not I restriction endonuclease cleavage sites.

Nucleic Acid Molecules

Unless otherwise indicated, all nucleotide sequences determined by sequencing a DNA molecule herein were determined using an automated DNA sequencer (such as the Model 373 from Applied Biosystems, Inc.), and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

Using the information provided herein, such as the nucleic acid sequence set out in SEQ ID NO:1, a nucleic acid molecule of the present invention encoding a TR10 polypeptide may be obtained using standard cloning and screening procedures, such as those for cloning cDNAs using mRNA as starting material. Illustrative of the invention, the nucleic acid molecule described in SEQ ID NO:1 was discovered in a cDNA library derived from keratinocytes. The gene of the present invention has also been identified in cDNA libraries from the following tissues: fetal liver, peripheral blood lymphocytes (PBL), lung, kidney, small intestine, colon, endothelial cells, and monocyte activated tissue. Furthermore, the following cancer cell lines express TR10: Hela cell S3, SW480 (colorectal adenocarcinoma), and A549 (lung carcinoma).

The determined nucleotide sequence of the TR10 cDNA of SEQ ID NO:1 contains an open reading frame encoding a protein of about 331 amino acid residues, with a predicted leader sequence of about 55 amino acid residues, and a deduced molecular weight of about 42 kDa. The amino acid sequence of the predicted mature TR10 receptor is shown in SEQ ID NO:2 from amino acid residue about 1 to residue about 331. Of known members of the TNF receptor family, the TR10 polypeptide of the invention shares the greatest degree of homology with human DR4 (See FIGS. 2A–2B), including significant sequence homology over multiple cysteine rich domains.

Owing to the sequence homology exhibited between TR10 and DR4 (and other death domain containing receptors), it was immediately recognized that TR10 would likely also bind to TRAIL. The cytoplasmic domain, interestingly, contains only a partial (or truncated) death domain. As described in Example 5, below, TR10 binds TRAIL but does not appear to cause cell death. TR10 binding of TRAIL, to the contrary, antagonizes apoptosis. Such antagonistic effect on TRAIL induced apoptosis can be achieved both through ectopic expression of TR10 and through exogenous administration of soluble TR10.

To examine the tissue distribution of TR10, Northern blot analysis was performed. A single transcript was detected in multiple human tissues at varying levels of expression, including, heart, lung, brain, placenta, liver, skeletal muscle, kidney, pancreas, spleen, thymus, prostate, testis, ovary, small intestine, colon, PBLs, lymph node, bone marrow and fetal liver. TR10 expression was not observed in most cancer cell lines tested. See Example 4, below.

As indicated, the present invention also provides the mature form(s) of the TR10 receptor of the present invention. According to the signal hypothesis, proteins secreted by mammalian cells have a signal or secretory leader sequence which is cleaved from the mature protein once export of the growing protein chain across the rough endoplasmic reticulum has been initiated. Most mammalian cells and even insect cells cleave secreted proteins with the same specificity. However, in some cases, cleavage of a secreted protein is not entirely uniform, which results in two or more mature species on the protein. Further, it has long been known that the cleavage specificity of a secreted protein is ultimately determined by the primary structure of the complete protein, that is, it is inherent in the amino acid sequence of the polypeptide.

Therefore, the present invention provides a nucleotide sequence encoding the mature TR10 polypeptide having the amino acid sequence encoded by the cDNA clone contained in the host identified as ATCC Deposit No. 209040, and as shown in FIG. 1 (SEQ ID NO:2). By the mature TR10 protein having the amino acid sequence encoded by the cDNA clones contained in the host identified as ATCC Deposit No. 209040 is meant the mature form(s) of the TR10 receptor produced by expression in a mammalian cell (e.g., COS cells, as described below) of the complete open reading frame encoded by the human DNA sequence of the clone contained in the vector in the deposited host. As indicated below, the mature TR10 receptor having the amino acid sequence encoded by the cDNA clone contained in ATCC Deposit No. 209040, may or may not differ from the predicted mature TR10 protein shown in SEQ ID NO:2 (amino acids from about 1 to about 331) depending on the accuracy of the predicted cleavage site based on computer analysis.

Methods for predicting whether a protein has a secretory leader as well as the cleavage point for that leader sequence are available. For instance, the method of McGeoch (*Virus Res.* 3:271–286 (1985)) and von Heinje (*Nucleic Acids Res.* 14:4683–4690 (1986)) can be used. The accuracy of predicting the cleavage points of known mammalian secretory proteins for each of these methods is in the range of 75–80%. von Heinje, supra. However, the two methods do not always produce the same predicted cleavage point(s) for a given protein.

In the present case, the predicted amino acid sequence of the complete TR10 polypeptide of the present invention was analyzed by a computer program ("PSORT"). See K. Nakai and M. Kanehisa, *Genomics* 14:897–911 (1992). PSORT is an expert system for predicting the cellular location of a protein based on the amino acid sequence. As part of this computational prediction of localization, the methods of McGeoch and von Heinje are incorporated. The analysis by the PSORT program predicted the cleavage site between amino acids −1 and 1 in SEQ ID NO:2. Thereafter, the complete amino acid sequences were further analyzed by visual inspection, applying a simple form of the (−1,−3) rule of von Heinje. von Heinje, supra. Thus, the leader sequence for the TR10 protein is predicted to consist of amino acid residues from about −55 to about −1 in SEQ ID NO:2, while the mature TR10 protein is predicted to consist of residues from about 1–331 in SEQ ID NO:2.

As one of ordinary skill would appreciate, due to the possibilities of sequencing errors, as well as the variability of cleavage sites for leaders in different known proteins, the predicted TR10 polypeptide encoded by the deposited cDNA comprises about 386 amino acids, but may be anywhere in the range of 376–396 amino acids; and the predicted leader sequence of this protein is about 55 amino acids, but may be anywhere in the range of about 45 to about 65 amino acids.

As indicated, nucleic acid molecules of the present invention may be in the form of RNA, such as mRNA, or in the form of DNA, including, for instance, cDNA and genomic DNA obtained by cloning or produced synthetically. The DNA may be double-stranded or single-stranded. Single-stranded DNA may be the coding strand, also known as the sense strand, or it may be the non-coding strand, also referred to as the anti-sense strand.

By "isolated" nucleic acid molecule(s) is intended a nucleic acid molecule, DNA or RNA, which has been removed from its native environment For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically.

Isolated nucleic acid molecules of the present invention include DNA molecules comprising an open reading frame (ORF) shown in SEQ ID NO:1; DNA molecules comprising the coding sequence for the mature TR10 protein; and DNA molecules which comprise a sequence substantially different from those described above, but which, due to the degeneracy of the genetic code, still encode the TR10 protein. Of course, the genetic code is well known in the art. Thus, it would be routine for one skilled in the art to generate such degenerate variants.

In addition, the invention provides nucleic acid molecules having nucleotide sequences related to extensive portions of SEQ ID NO:1 which have been determined from the following related cDNA clones: HSABD50R (SEQ ID NO:7), HGBDL20R(SEQ ID NO:8), and HELDL61R (SEQ ID NO:9), and AA150849 (SEQ ID NO:15).

In another aspect, the invention provides isolated nucleic acid molecules encoding the TR10 polypeptide having an amino acid sequence as encoded by the cDNA clone contained in the plasmid deposited as ATCC Deposit No. 209040 on May 15, 1997. In a further embodiment, nucleic acid molecules are provided that encode the mature TR10 polypeptide or the full length TR10 polypeptide lacking the N-terminal methionine. The invention further provides an isolated nucleic acid molecule having the nucleotide sequence shown in SEQ ID NO:1 or the nucleotide sequence of the TR10 cDNA contained in the above-described deposited clone, or a nucleic acid molecule having a sequence complementary to one of the above sequences. Such isolated molecules, particularly DNA molecules, are useful as probes for gene mapping by in situ hybridization with chromosomes, and for detecting expression of the TR10 gene in human tissue, for instance, by Northern blot analysis.

The present invention is further directed to fragments of the isolated nucleic acid molecules described herein. By a fragment of an isolated DNA molecule having the nucleotide sequence of the deposited cDNA or the nucleotide sequence shown in SEQ ID NO:1 is intended DNA fragments at least about 15 nt, and more preferably at least 20 nt, still more preferably at least about 30 nt, and even more preferably, at least about 40 nt in length which are useful as diagnostic probes and primers as discussed herein. Of course, larger fragments 50–1500 nt in length are also useful according to the present invention, as are fragments corresponding to most, if not all, of the nucleotide sequence of the deposited cDNA or as shown in SEQ ID NO:1. By a fragment at least 20 nt in length, for example, is intended fragments which include 20 or more contiguous bases from the nucleotide sequence of the deposited cDNA or the nucleotide sequence as shown in SEQ ID NO:1.

Preferred nucleic acid fragments of the present invention include nucleic acid molecules encoding: a polypeptide comprising the TR10 receptor extracellular domain (amino acid residues from about 56 to about 212 in FIGS. 1A–F or from about 1 to about 157 in SEQ ID NO:2); a polypeptide comprising the TR10 transmembrane domain (amino acid residues from about 213 to about 230 in FIGS. 1A–F or from about 158 to about 175 in SEQ ID NO:2); a polypeptide comprising the TR10 intracellular domain (amino acid residues from about 231 to about 386 in FIGS. 1A–F or from about 176 to about 331 in SEQ ID NO:2); and a polypeptide comprising the incomplete TR10 death domain (amino acid residues from about 353 to about 363 in FIG. 1 or from about 298 to about 308 in SEQ ID NO:2). Since the location of these domains have been predicted by computer analysis, one of ordinary skill would appreciate that the amino acid residues constituting these domains may vary slightly (e.g., by about 1 to 15 amino acid residues) depending on the criteria used to define each domain.

Preferred nucleic acid fragments of the invention encode a full-length TR10 polypeptide lacking the nucleotides encoding the amino terminal methionine (nucleotides 109–111 in SEQ ID NO:1), as it is known that the methionine is cleaved naturally and such sequences may be useful in genetically engineering TR10 expression vectors. Polypeptides encoded by such polynucleotides are also contemplated by the invention.

Preferred nucleic acid fragments of the present invention further include nucleic acid molecules encoding epitope-bearing portions of the TR10 receptor protein. In particular, such nucleic acid fragments of the present invention include nucleic acid molecules encoding: a polypeptide comprising amino acid residues from about 57 to about 113 in FIGS. 1A–F (corresponding to about amino acid 2 to about 58 in SEQ ID NO:2); a polypeptide comprising amino acid residues from about 130 to about 197 in FIGS. 1A–F (corresponding to about amino acid 75 to about 142 in SEQ ID NO:2); and a polypeptide comprising amino acid residues from about 250 to about 283 in FIGS. 1A–F (corresponding to about amino acid 195 to about 228 in SEQ ID NO:2). The inventors have determined that the above polypeptide fragments are antigenic regions of the TR10 protein. Methods for determining other such epitope-bearing portions of the TR10 protein are described in detail below.

In another aspect, the invention provides an isolated nucleic acid molecule comprising a polynucleotide which hybridizes under stringent hybridization conditions to a portion of the polynucleotide in a nucleic acid molecule of the invention described above, for instance, the cDNA clones contained in ATCC Deposit No. 209040. By "stringent hybridization conditions" is intended overnight incubation at 42° C. in a solution comprising: 50% formamide, 5×SSC (750 mM NaCl, 75 mM trisodium citrate), 50 mM sodium phosphate (pH 7.6), 5×Denhardt's solution, 10% dextran sulfate, and 20 g/ml denatured, sheared salmon sperm DNA, followed by washing the filters in 0.1×SSC at about 65° C.

By a polynucleotide which hybridizes to a "portion" of a polynucleotide is intended a polynucleotide (either DNA or RNA) hybridizing to at least about 15 nucleotides (nt), and more preferably at least about 20 nt, still more preferably at least about 30 nt, and even more preferably about 30–70 nt of the reference polynucleotide. These are useful as diagnostic probes and primers as discussed above and in more detail below.

By a portion of a polynucleotide of "at least 20 nt in length," for example, is intended 20 or more contiguous nucleotides from the nucleotide sequence of the reference polynucleotide (e.g., the deposited cDNA or the nucleotide sequence as shown in SEQ ID NO:1).

Of course, a polynucleotide which hybridizes only to a poly A sequence (such as the 3' terminal poly(A) tract of the TR10 cDNA shown in SEQ ID NO:1), or to a complementary stretch of T (or U) resides, would not be included in a polynucleotide of the invention used to hybridize to a portion of a nucleic acid of the invention, since such a polynucleotide would hybridize to any nucleic acid molecule containing a poly (A) stretch or the complement thereof (e.g., practically any double-stranded cDNA clone).

As indicated, nucleic acid molecules of the present invention which encode a TR10 polypeptide may include, but are not limited to the coding sequence for the mature polypeptide, by itself; the coding sequence for the mature polypeptide and additional sequences, such as those encoding a leader or secretary sequence, such as a pre-, or pro- or prepro- protein sequence; the coding sequence of the mature polypeptide, with or without the aforementioned additional coding sequences, together with additional, non-coding sequences, including for example, but not limited to introns and non-coding 5' and 3' sequences, such as the transcribed, non-translated sequences that play a role in transcription, mRNA processing—including splicing and polyadenylation signals, for example—ribosome binding and stability of mRNA; additional coding sequence which codes for additional amino acids, such as those which provide additional functionalities. Thus, for instance, the polypeptide may be fused to a marker sequence, such as a peptide, which facilitates purification of the fused polypeptide. In certain preferred embodiments of this aspect of the invention, the marker sequence is a hexa-histidine peptide, such as the tag provided in a pQE vector (Qiagen, Inc.), among others, many of which are commercially available. As described in Gentz et al., *Proc. Natl. Acad. Sci. USA* 86: 821–824 (1989), for instance, hexa-histidine provides for convenient purification of the fusion protein. The "HA" tag is another peptide useful for purification which corresponds to an epitope derived from the influenza hemagglutinin protein, which has been described by Wilson et al., *Cell* 37:767–778 (1984). As discussed below, other such fusion proteins include the TR10 receptor fused to Fc at the N- or C-terminus.

The present invention further relates to variants of the nucleic acid molecules of the present invention, which encode portions, analogs, or derivatives of the TR10 receptor. Variants may occur naturally, such as a natural allelic variant. By an "allelic variant" is intended one of several alternate forms of a gene occupying a given locus on a chromosome of an organism. *Genes II*, Lewin, B., ed., John Wiley & Sons, New York (1985). Non-naturally occurring variants may be produced using art-known mutagenesis techniques.

Such variants include those produced by nucleotide substitutions, deletions or additions which may involve one or more nucleotides. The variants may be altered in coding or non-coding regions or both. Alterations in the coding regions may produce conservative or non-conservative amino acid substitutions, deletions, or additions. Especially preferred among these are silent substitutions, additions, and deletions, which do not alter the properties and activities of the TR10 receptor or portions thereof. Also especially preferred in this regard are conservative substitutions.

Further embodiments of the invention include isolated nucleic acid molecules comprising a polynucleotide having a nucleotide sequence at least 90% identical, and more preferably at least 95%, 96%, 97%, 98%, or 99% identical to: (a) a nucleotide sequence encoding the polypeptide having the amino acid sequence in SEQ ID NO:2; (b) a nucleotide sequence encoding the polypeptide having the amino acid sequence in SEQ ID NO:2, but lacking the amino terminal methionine; (c) a nucleotide sequence encoding the polypeptide having the amino acid sequence at positions about 1 to about 331 in SEQ ID NO:2; (d) a nucleotide sequence encoding the polypeptide having the amino acid sequence encoded by the cDNA clone contained in ATCC Deposit No. 209040; (e) a nucleotide sequence encoding the mature TR10 polypeptide having the amino acid sequence encoded by the cDNA clone contained in ATCC Deposit No. 209040; (f) a nucleotide sequence encoding the TR10 receptor extracellular domain; (g) a nucleotide sequence encoding the TR10 receptor transmembrane domain; (h) a nucleotide sequence encoding the TR10 receptor intracellular domain;

(i) a nucleotide sequence encoding the TR10 receptor extracellular and intracellular domains with all or part of the transmembrane domain deleted; (j) a nucleotide sequence encoding the TR10 receptor partial death domain; and (k) a nucleotide sequence complementary to any of the nucleotide sequences in (a), (b), (c), (d), (e), (f), (g), (h), (i), or (j) above.

By a polynucleotide having a nucleotide sequence at least, for example, 95% "identical" to a reference nucleotide sequence encoding a TR10 polypeptide is intended that the nucleotide sequence of the polynucleotide is identical to the reference sequence except that the polynucleotide sequence may include up to five point mutations per each 100 nucleotides of the reference nucleotide sequence encoding the TR10 polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 90%, 95%, 96%, 97%, 98% or 99% identical to, for instance, the nucleotide sequence shown in SEQ ID NO:1 or to the nucleotide sequence of the deposited cDNA clone can be determined conventionally using known computer programs such as the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman, *Advances in Applied Mathematics* 2: 482489 (1981), to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

The present application is directed to nucleic acid molecules at least 90%, 95%, 96%, 97%, 98%, or 99% identical to the nucleic acid sequence shown in SEQ ID NO:1, or to the nucleic acid sequence of the deposited cDNA, irrespective of whether they encode a polypeptide having TR10 receptor activity. This is because even where a particular nucleic acid molecule does not encode a polypeptide having TR10 activity, one of skill in the art would still know how to use the nucleic acid molecule, for instance, as a hybridization probe or a polymerase chain reaction (PCR) primer. Uses of the nucleic acid molecules of the present invention that do not encode a polypeptide having TR10 receptor activity include, inter alia: (1) isolating the TR10 receptor gene or allelic variants thereof in a cDNA library; (2) in situ hybridization (e.g., "FISH") to metaphase chromosomal spreads to provide precise chromosomal location of the TR10 receptor gene, as described in Verma et al., *Human Chromosomes: A Manual of Basic Techniques*, Pergamon Press, New York (1988); and (3) Northern Blot analysis for detecting TR10 receptor mRNA expression in specific tissues.

Preferred, however, are nucleic acid molecules having sequences at least 90%, 95%, 96%, 97%, 98% or 99% identical to the nucleic acid sequence shown in SEQ ID NO:1, or to the nucleic acid sequence of the deposited cDNA which do, in fact, encode a polypeptide having TR10 receptor activity. By "a polypeptide having TR10 receptor activity" is intended polypeptides exhibiting activity similar, but not necessarily identical, to an activity of the TR10 receptor of the invention (either the full-length protein or, preferably, the mature protein), as measured in a particular biological assay. For example, TR10 receptor activity can be measured using the cell death assays performed essentially as previously described (A. M. Chinnaiyan et al., *Cell* 81: 505–512 (1995); M. P. Boldin et al., *J. Biol. Chem.* 270:7795–8 (1995); F. C. Kischkel et al., *EMBO* 14:5579–5588 (1995); A. M. Chinnaiyan et al., *J. Biol. Chem.* 271: 4961–4965 (1996)) and as set forth in Example 5, below. In MCF7 cells, plasmids encoding full-length TR10 or a candidate death domain containing receptor are co-transfected with the pLantern reporter construct encoding green fluorescent protein. Nuclei of cells transfected with TR10 will exhibit apoptotic morphology as assessed by DAPI staining. Similar to TNFR-1 and Fas/APO-1 (M. Muzio et al., *Cell* 85:817–827 (1996); M. P. Boldin et al., *Cell* 85:803–815 (1996); M. Tewari et al., *J. Biol. Chem.* 270:3255–60 (1995)), TR10-induced apoptosis is blocked by the inhibitors of ICE-like proteases, CrmA and z-VAD-fmk. In addition, apoptosis induced by TR10 is also blocked by dominant negative versions of FADD (FADD-DN) or FLICE (FLICE-DN/MACHa1C360S).

Of course, due to the degeneracy of the genetic code, one of ordinary skill in the art will immediately recognize that a large number of the nucleic acid molecules having a sequence at least 90%, 95%, 96%, 97%, 98%, or 99% identical to the nucleic acid sequence of the deposited cDNA or the nucleic acid sequence shown in SEQ ID NO:1 will encode a polypeptide "having TR10 receptor activity." In fact, since degenerate variants of these nucleotide sequences all encode the same polypeptide, this will be clear to the skilled artisan even without performing the above described comparison assay. It will be further recognized in the art that, for such nucleic acid molecules that are not degenerate variants, a reasonable number will also encode a polypeptide having TR10 receptor activity. This is because the skilled artisan is fully aware of amino acid substitutions that are either less likely or not likely to significantly effect protein function (e.g., replacing one aliphatic amino acid with a second aliphatic amino acid).

For example, guidance concerning how to make phenotypically silent amino acid substitutions is provided in J. U. Bowie et al., "Deciphering the Message in Protein Sequences: Tolerance to Amino Acid Substitutions," *Science* 247:1306–1310 (1990), wherein the authors indicate that proteins are surprisingly tolerant of amino acid substitutions.

Polynucleotide Assays

This invention is also related to the use of TR10 polynucleotides to detect complementary polynucleotides such as, for example, as a diagnostic reagent. Detection of a mutated form of TR10 associated with a dysfunction will provide a diagnostic tool that can add or define a diagnosis of a disease or susceptibility to a disease which results from under-expression over-expression or altered expression of TR10 or a soluble form thereof, such as, for example, tumors or autoimmune disease.

Individuals carrying mutations in the TR10 gene may be detected at the DNA level by a variety of techniques. Nucleic acids for diagnosis may be obtained from a patient's cells, such as from blood, urine, saliva, tissue biopsy and autopsy material. The genomic DNA may be used directly for detection or may be amplified enzymatically by using PCR prior to analysis. (Saiki et al., *Nature* 324:163–166 (1986)). RNA or cDNA may also be used in the same ways. As an example, PCR primers complementary to the nucleic acid encoding TR10 can be used to identify and analyze TR10 expression and mutations. For example, deletions and insertions can be detected by a change in size of the amplified product in comparison to the normal genotype. Point mutations can be identified by hybridizing amplified DNA to radiolabeled TR10 RNA or alternatively, radiolabeled TR10 antisense DNA sequences. Perfectly matched sequences can be distinguished from mismatched duplexes by RNase A digestion or by differences in melting temperatures.

Sequence differences between a reference gene and genes having mutations also may be revealed by direct DNA sequencing. In addition, cloned DNA segments may be employed as probes to detect specific DNA segments. The sensitivity of such methods can be greatly enhanced by appropriate use of PCR or another amplification method. For example, a sequencing primer is used with double-stranded PCR product or a single-stranded template molecule generated by a modified PCR. The sequence determination is performed by conventional procedures with radiolabeled nucleotide or by automatic sequencing procedures with fluorescent-tags.

Genetic testing based on DNA sequence differences may be achieved by detection of alteration in electrophoretic mobility of DNA fragments in gels, with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al., *Science* 230:1242 (1985)).

Sequence changes at specific locations also may be revealed by nuclease protection assays, such as RNase and S1 protection or the chemical cleavage method (e.g., Cotton et al., *Proc. Natl. Acad. Sci. USA* 85: 4397–4401 (1985)).

Thus, the detection of a specific DNA sequence may be achieved by methods such as hybridization, RNase protection, chemical cleavage, direct DNA sequencing or the use of restriction enzymes, (e.g., restriction fragment length polymorphisms ("RFLP") and Southern blotting of genomic DNA.

In addition to more conventional gel-electrophoresis and DNA sequencing, mutations also can be detected by in situ analysis.

Vectors and Host Cells

The present invention also relates to vectors which include the isolated DNA molecules of the present invention, host cells which are genetically engineered with the recombinant vectors of the invention and the production of TR10 polypeptides or fragments thereof by recombinant techniques.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

The DNA insert should be operatively linked to an appropriate promoter, such as the phage lambda PL promoter, the *E. coli* lac, trp and tac promoters, the SV40 early and late promoters and promoters of retroviral LTRs, to name a few. Other suitable promoters will be known to the skilled artisan. The expression constructs will further contain sites for transcription initiation, termination and, in the transcribed region, a ribosome binding site for translation. The coding portion of the mature transcripts expressed by the constructs will preferably include a translation initiating at the beginning and a termination codon (UAA, UGA or UAG) appropriately positioned at the end of the polypeptide to be translated.

As indicated, the expression vectors will preferably include at least one selectable marker. Such markers include dihydrofolate reductase or neomycin resistance for eukaryotic cell culture and tetracycline or ampicillin resistance genes for culturing in *E. coli* and other bacteria. Representative examples of appropriate hosts include, but are not limited to, bacterial cells, such as *E. coli*, Streptomyces and *Salmonella typhimurium* cells; fungal cells, such as yeast cells; insect cells such as Drosophila S2 and Spodoptera Sf9 cells; animal cells such as CHO, COS and Bowes melanoma cells; and plant cells. Appropriate culture mediums and conditions for the above-described host cells are known in the art.

Among vectors preferred for use in bacteria include pQE70, pQE60 and pQE-9, available from Qiagen; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Among preferred eukaryotic vectors are pWLNEO, pSV2CAT, pOG44, pXT1 and pSG available from Stratagene; and pSVK3, pBPV, pMSG and pSVL available from Pharmacia. Other suitable vectors will be readily apparent to the skilled artisan.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al., *Basic Methods In Molecular Biology* (1986).

The polypeptide may be expressed in a modified form, such as a fusion protein, and may include not only secretion signals but also additional heterologous functional regions. Thus, for instance, a region of additional amino acids, particularly charged amino acids, may be added to the N-terminus of the polypeptide to improve stability and persistence in the host cell, during purification or during subsequent handling and storage. Also, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art. A preferred fusion protein comprises a heterologous region from immunoglobulin that is useful to solubilize proteins. For example, EP-A-O 464 533 (Canadian counterpart 2045869) discloses fusion proteins comprising various portions of constant region of immunoglobin molecules together with another human protein or part thereof. In many cases, the Fc part in a fusion protein is thoroughly advantageous for use in therapy and diagnosis and thus results, for example, in improved pharmacokinetic properties (EP-A 0232 262). On the other hand, for some uses, it would be desirable to be able to delete the Fc part after the fusion protein has been expressed, detected and purified in the advantageous manner described. This is the case when the Fc portion proves to be a hindrance to use in therapy and diagnosis, for example, when the fusion protein is to be used as an antigen for immunizations. In drug discovery, for example, human proteins, such as the hIL5-receptor, have been fused with Fc portions for the purpose of high-throughput screening assays to identify antagonists of hIL-5. See, D. Bennett et al., *Journal of Molecular Recognition* 8:52–58 (1995) and K. Johanson et al., *The Journal of Biological Chemistry* 270:16:9459–9471 (1995).

The TR10 receptor can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification.

Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or non-glycosylated. In addition, polypeptides of the invention may also include an initial modified methionine residue, in some cases as a result of host-mediated processes.

TR10 receptor polynucleotides and polypeptides may be used in accordance with the present invention for a variety of applications, particularly those that make use of the chemical and biological properties of TR10. Among these are applications in treatment of tumors, resistance to parasites, bacteria and viruses, to induce proliferation of T-cells, endothelial cells and certain hematopoietic cells, to treat restenosis, graft vs. host disease, to regulate anti-viral responses and to prevent certain autoimmune diseases after stimulation of TR10 by an agonist. Additional applications relate to diagnosis and to treatment of disorders of cells, tissues and organisms. These aspects of the invention are discussed further below.

TR10 Receptor Polypeptides and Fragments

The invention further provides an isolated TR10 polypeptide having the amino acid sequence encoded by the deposited cDNA, or the amino acid sequence in SEQ ID NO:2, or a peptide or polypeptide comprising a portion of the above polypeptides.

It will be recognized in the art that some amino acid sequences of TR10 can be varied without significant effect on the structure or function of the protein. If such differences in sequence are contemplated, it should be remembered that there will be critical areas on the protein which determine activity. Thus, the invention further includes variations of the TR10 receptor, which show substantial TR10 receptor activity or which include regions of TR10 proteins, such as the protein portions discussed below. Such mutants include deletions, insertions, inversions, repeats, and type substitutions. As indicated above, guidance concerning which amino acid changes are likely to be phenotypically silent can be found in J. U. Bowie et al., *Science* 247: 1306–1310 (1990).

Thus, the fragment, derivative, or analog of the polypeptide of SEQ ID NO:2, or that encoded by the deposited cDNA, may be (i) one in which at least one or more of the amino acid residues are substituted with a conserved or non-conserved amino acid residue (preferably a conserved amino acid residue(s), and more preferably at least one but less than ten conserved amino acid residues) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as an IgG Fc fusion region peptide or leader or secretory sequence or a sequence which is employed for purification of the mature polypeptide or a proprotein sequence. Such fragments, derivatives and analogs are deemed to be within the scope of those skilled in the art from the teachings herein.

Of particular interest are substitutions of charged amino acids with another charged amino acid and with neutral or negatively charged amino acids. The latter results in proteins with reduced positive charge to improve the characteristics of the TR10 receptor protein. The prevention of aggregation is highly desirable. Aggregation of proteins not only results in a loss of activity but can also be problematic when preparing pharmaceutical formulations, because they can be immunogenic. (Pinckard et al., *Clin Exp. Immunol.* 2:331–340 (1967); Robbins et al., *Diabetes* 36:838–845 (1987); Cleland et al. *Crit. Rev. Therapeutic Drug Carrier Systems* 10:307–377 (1993)).

The replacement of amino acids can also change the selectivity of binding to cell surface receptors. Ostade et al., *Nature* 361:266–268 (1993), describes certain mutations resulting in selective binding of TNF- to only one of the two known types of TNF receptors. Thus, the TR10 receptor of the present invention may include one or more amino acid substitutions, deletions, or additions, either from natural mutations or human manipulation.

As indicated, changes are preferably of a minor nature, such as conservative amino acid substitutions that do not significantly affect the folding or activity of the protein (see Table 1).

TABLE 1

Conservative Amino Acid Substitutions

| | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

Amino acids in the TR10 protein of the present invention that are essential for function can be identified by methods known in the art, such as site-directed mutagenesis or alanine-scanning mutagenesis (Cunningham and Wells, *Science* 244:1081–1085 (1989)). The latter procedure introduces single alanine mutations at every residue in the molecule. The resulting mutant molecules are then tested for biological activity such as receptor binding or in vitro proliferative activity. Sites that are critical for ligand-receptor binding can also be determined by structural analysis such as crystallization, nuclear magnetic resonance or photoaffinity labeling (Smith et al., *J. Mol. Biol.* 224:899–904 (1992) and de Vos et al. *Science* 255:306–312 (1992)).

The polypeptides of the present invention are preferably provided in an isolated form. By "isolated polypeptide" is intended a polypeptide removed from its native environment. Thus, a polypeptide produced and/or contained within a recombinant host cell is considered isolated for purposes of the present invention. Also intended as an "isolated polypeptide" are polypeptides that have been purified, partially or substantially, from a recombinant host cell. For example, a recombinantly produced version of the TR10 polypeptide can be substantially purified by the one-step method described in Smith and Johnson, *Gene* 67:31–40 (1988).

The polypeptides of the present invention include the polypeptide encoded by the deposited cDNA including the leader; the mature polypeptide encoded by the deposited cDNA minus the leader (i.e., the mature protein); a polypeptide comprising amino acids about −55 to about 331 in SEQ ID NO:2; a polypeptide comprising amino acids about −54 to about 331 in SEQ ID NO:2; a polypeptide comprising amino acids about 1 to about 331 in SEQ ID NO:2; a polypeptide comprising the extracellular domain; a polypeptide comprising the transmembrane domain; a polypeptide comprising the intracellular domain; a polypeptide comprising the extracellular and intracellular domains with all or part of the transmembrane domain deleted; and a polypeptide comprising the partial death domain; as well as polypeptides which are at least 80% identical, more preferably at least 90% or 95% identical, still more preferably at least 96%, 97%, 98%, or 99% identical to the polypeptides described above, and also include portions of such polypeptides with at least 30 amino acids and more preferably at least 50 amino acids.

By a polypeptide having an amino acid sequence at least, for example, 95% "identical" to a reference amino acid sequence of a TR10 polypeptide is intended that the amino acid sequence of the polypeptide is identical to the reference sequence except that the polypeptide sequence may include up to five amino acid alterations per each 100 amino acids of the reference amino acid of the TR10 receptor. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 90%, 95%, 96%, 97%, 98%, or 99% identical to, for instance, the amino acid sequence shown in SEQ ID NO:2, or to the amino acid sequence encoded by the deposited cDNA clone, can be determined conventionally using known computer programs such the Bestfit program (Wisconsin Sequence Analysis Package, Version 8 for Unix, Genetics Computer Group, University Research Park, 575 Science Drive, Madison, Wis. 53711). When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

Particularly, N-terminal deletions of the TR10 polypeptide can be described by the general formula m-157, where m is a number from 1–156, corresponding to the position of amino acid identified in SEQ ID NO:2. Preferably, N-terminal deletions of the TR10 polypeptide of the invention shown as SEQ ID NO:2 include polypeptides comprising the amino acid sequence of residues: T-2 to Y-157; I-3 to Y-157; P-4 to Y-157; R-5 to Y-157; Q-6 to Y-157; D-7 to Y-157; E-8 to Y-157; V-9 to Y-157; P-10 to Y-157; Q-11 to Y-157; Q-12 to Y-157; T-13 to Y-157; V-14 to Y-157; A-15 to Y-157; P-16 to Y-157; Q-17 to Y-157; Q-18 to Y-157; Q-19 to Y-157; R-20 to Y-157; R-21 to Y-157; S-22 to Y-157; L-23 to Y-157; K-24 to Y-157; E-25 to Y-157; E-26 to Y-157; E-27 to Y-157; C-28 to Y-157; P-29 to Y-157; A-30 to Y-157; G-31 to Y-157; S-32 to Y-157; H-33 to Y-157; R-34 to Y-157; S-35 to Y-157; E-36 to Y-157; Y-37 to Y-157; T-38 to Y-157; G-39 to Y-157; A-40 to Y-157; C-41 to Y-157; N-42 to Y-157; P-43 to Y-157; C-44 to Y-157; T-45 to Y-157; E-46 to Y-157; G-47 to Y-157; V-48 to Y-157; D-49 to Y-157; Y-50 to Y-157; T-51 to Y-157; I-52 to Y-157; A-53 to Y-157; S-54 to Y-157; N-55 to Y-157; N-56 to Y-157; L-57 to Y-157; P-58 to Y-157; S-59 to Y-157; C-60 to Y-157; L-61 to Y-157; L-62 to Y-157; C-63 to Y-157; T-64 to Y-157; V-65 to Y-157; C-66 to Y-157; K-67 to Y-157; S-68 to Y-157; G-69 to Y-157; Q-70 to Y-157; T-71 to Y-157; N-72 to Y-157; K-73 to Y-157; S-74 to Y-157; S-75 to Y-157; C-76 to Y-157; T-77 to Y-157; T-78 to Y-157; T-79 to Y-157; R-80 to Y-157; D-81 to Y-157; T-82 to Y-157; V-83 to Y-157; C-84 to Y-157; Q-85 to Y-157; C-86 to Y-157; E-87 to Y-157; K-88 to Y-157; G-89 to Y-157; S-90 to Y-157; F-91 to Y-157; Q-92 to Y-157; D-93 to Y-157; K-94 to Y-157; N-95 to Y-157; S-96 to Y-157; P-97 to Y-157; E-98 to Y-157; M-99 to Y-157; C-100 to Y-157; R-101 to Y-157; T-102 to Y-157; C-103 to Y-157; R-104 to Y-157; T-105 to Y-157; G-106 to Y-157; C-107 Y-157; P-108 to Y-157; R-109 to Y-157; G-110 to Y-157; M-111 to Y-157; V-112 to Y-157; K-113 to Y-157; V-114 to Y-157; S-115 to Y-157; N-116 to Y-157; C-117 to Y-157; to T-118 Y-157; P-119 to Y-157; R-120 to Y-157; S-121 to Y-157; D-122 to Y-157; I-123 to Y-157; K-124 to Y-157; C-125 to Y-157; K-126 to Y-157; N-127 to Y-157; E-128 to Y-157; S-129 to Y-157; A-130 to Y-157; A-131 to Y-157; S-132 to Y-157; S-133 to Y-157; T-134 to Y-157; G-135 to Y-157; K-136 to Y-157; T-137 to Y-157; P-138 to Y-157; A-139 to Y-157; A-140 to Y-157; E-141 to Y-157; E-142 to Y-157; T-143 to Y-157; V-144 to Y-157; T-145 to Y-157; T-146 to Y-157; I-147 to Y-157; L-148 to Y-157; G-149 to Y-157; M-150 to Y-157; L-151 to Y-157; A-152 to Y-157; of SEQ ID NO:2.

Moreover, C-terminal deletions of the TR10 polypeptide can also be described by the general formula 1-n, where n is a number from 2–156, corresponding to the position of amino acid identified in SEQ ID NO:2. Preferably, C-terminal deletions of the TR10 polypeptide of the invention shown as SEQ ID NO:2 include polypeptides comprising the amino acid sequence of residues: A-1 to H-156; A-1 to Y-155; A-1 to P-154; A-1 to S-153; A-1 to A-152; A-1 to L-151; A-1 to M-150; A-1 to G-149; A-1 to L-148; A-1 to I-147; A-1 to T-146; A-1 to T-145; A-1 to V-144; A-1 to T-143; A-1 to E-142; A-1 to E-141; A-1 to A-140; A-1 to A-139; A-1 to P-138; A-1 to T-137; A-1 to K-136; A-1 to G-135; A-1 to T-134; A-1 to S-133; A-1 to S-132; A-1 to A-131; A-1 to A-130; A-1 to S-129; A-1 to E-128; A-1 to N-127; A-1 to K-126; A-1 to C-125; A-1 to K-124; A-1 to I-123; A-1 to D-122; A-1 to S-121; A-1 to R-120; A-1 to P-119; A-1 to T-118; A-1 to C-117; A-1 to N-116; A-1 to S-115; A-1 to V-114; A-1 to K-113; A-1 to V-112; A-1 to M-111; A-1 to G-110; A-1 to R-109; A-1 to P-108; A-1 to C-107; A-1 to G-106; A-1 to T-105; A-1 to R-104; A-1 to C-103; A-1 to T-102; A-1 to R-101; A-1 C-100; A-1 to M-99; A-1 to E-98; A-1 to P-97; A-1 to S-96; A-1 to N-95; A-1 to K-94; A-1 to D-93; A-1 to Q-92; A-1 to F-91; A-1 to S-90; A-1 to G-89; A-1 to K-88; A-1 to E-87; A-1 to C-86; A-1 to Q-85; A-1 to C-84; A-1 to V-83; A-1 to T-82; A-1 to D-81; A-1 to R-80; A-1 to T-79; A-1 to T-78; A-1 to T-77; A-1 to C-76; A-1 to S-75; A-1 to S-74; A-1 to K-73; A-1 to N-72; A-1 to T-71; A-1 to Q-70; A-1 to G-69; A-1 to S-68; A-1 to K-67; A-1 to C-66; A-1 to V-65; A-1 to T-64; A-1 to C-63; A-1 to L-62; A-1 to L-61; A-1 to C-60; A-1 to S-59; A-1 to P-58; A-1 to L-57; A-1 to N-56; A-1 to N-55; A-1 to S-54; A-1 to A-53; A-1 to I-52; A-1 to T-51; A-1 to Y-50; A-1 to D-49; A-1 to V-48; A-1 to G-47; A-1 to E-46; A-1 to T-45; A-1 to C-44; A-1 to P-43; A-1 to N-42; A-1 to C-41; A-1 to A-40; A-1 to G-39; A-1 to T-38; A-1 to Y-37; A-1 to E-36; A-1 to S-35; A-1 to R-34; A-1 to H-33; A-1 to S-32; A-1 to G-31; A-1 to A-30; A-1 to P-29; A-1 to C-28; A-1 to E-27; A-1 to E-26; A-1 to E-25; A-1 to K-24; A-1 to L-23; A-1 to S-22; A-1 to R-21; A-1 to R-20; A-1 to Q-19; A-1 to Q-18; A-1 to Q-17; A-1 to P-16; A-1 to A-15; to V-14; A-1 to T-13; A-1 to Q-12; A-1 to Q-11; A-1 to P-10; A-1 to V-9; A-1 to E-8; A-1 to D-7; of SEQ ID NO:2.

For example, any of the above listed N- or C-terminal deletions can be combined to produce a N- and C-terminal deleted TR10 polypeptide.

The invention also provides polypeptides having one or more amino acids deleted from both the amino and the carboxyl termini, which may be described generally as having residues n-m of SEQ ID NO:2, where n and m are integers as described above.

The polypeptide of the present invention could be used as a molecular weight marker on SDS-PAGE gels or on molecular sieve gel filtration columns using methods well known to those of skill in the art.

In another aspect, the invention provides a peptide or polypeptide comprising an epitope-bearing portion of a polypeptide of the invention. The epitope of this polypeptide portion is an immunogenic or antigenic epitope of a polypeptide described herein. An "immunogenic epitope" is defined as a part of a protein that elicits an antibody response when the whole protein is the immunogen. On the other hand, a region of a protein molecule to which an antibody can bind is defined as an "antigenic epitope." The number of immunogenic epitopes of a protein generally is less than the number of antigenic epitopes. See, for instance, Geysen et al., *Proc. Natl. Acad. Sci. USA* 81:3998–4002 (1983).

As to the selection of peptides or polypeptides bearing an antigenic epitope (i.e., that contain a region of a protein molecule to which an antibody can bind), it is well known in that art that relatively short synthetic peptides that mimic part of a protein sequence are routinely capable of eliciting an antiserum that reacts with the partially mimicked protein. See, for instance, J. G. Sutcliffe et al., "Antibodies That React With Predetermined Sites on Proteins," *Science* 219:660–666 (1983). Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals.

Antigenic epitope-bearing peptides and polypeptides of the invention are therefore useful to raise antibodies, including monoclonal antibodies, that bind specifically to a polypeptide of the invention. See, for instance, Wilson et al., *Cell* 37:767–778 (1984) at 777. Antigenic epitope-bearing peptides and polypeptides of the invention preferably contain a sequence of at least seven, more preferably at least nine, and most preferably between at least about 15 to about 30 amino acids contained within the amino acid sequence of a polypeptide of the invention.

Non-limiting examples of antigenic polypeptides or peptides that can be used to generate TR10 receptor-specific antibodies include: a polypeptide comprising amino acid residues from about 57 to about 113 in FIGS. 1A–F (2 to 58 in SEQ ID NO:2); a polypeptide comprising amino acid residues from about 130 to about 197 in FIGS. 1A–F (75 to 142 in SEQ ID NO:2); and a polypeptide comprising amino acid residues from about 250 to about 283 in FIGS. 1A–F (195 to 228 in SEQ ID NO:2). As indicated above, the inventors have determined that the above polypeptide fragments are antigenic regions of the TR10 receptor protein.

The epitope-bearing peptides and polypeptides of the invention may be produced by any conventional means. R. A. Houghten, "General Method for the Rapid Solid-phase Synthesis of Large Numbers of Peptides: Specificity of Antigen-Antibody Interaction at the Level of Individual Amino Acids," *Proc. Natl. Acad. Sci. USA* 82:5131–5135 (1985). This "Simultaneous Multiple Peptide Synthesis (SMPS)" process is further described in U.S. Pat. No. 4,631,211 to Houghten et al. (1986).

As one of skill in the art will appreciate, TR10 receptor polypeptides of the present invention and the epitope-bearing fragments thereof, described above, can be combined with parts of the constant domain of immunoglobulins (IgG), resulting in chimeric polypeptides. These fusion proteins facilitate purification and show an increased half-life in vivo. This has been shown, e.g., for chimeric proteins consisting of the first two domains of the human CD4-polypeptide and various domains of the constant regions of the heavy or light chains of mammalian immunoglobulins (EPA 394,827; Traunecker et al., *Nature* 331:84–86 (1988)). Fusion proteins that have a disulfide-linked dimeric structure due to the IgG part can also be more efficient in binding and neutralizing other molecules than the monomeric TR10 protein or protein fragment alone (Fountoulakis et al., *J. Biochem.* 270:3958–3964 (1995)).

Polypeptide Assays

The present invention also relates to diagnostic assays such as quantitative and diagnostic assays for detecting levels of TR10 receptor protein, or the soluble form thereof, in cells and tissues, including determination of normal and abnormal levels. Thus, for instance, a diagnostic assay in accordance with the invention for detecting over-expression of TR10, or soluble form thereof, compared to normal control tissue samples may be used to detect the presence of tumors, for example. Assay techniques that can be used to determine levels of a protein, such as a TR10 protein of the present invention, or a soluble form thereof, in a sample derived from a host are well-known to those of skill in the art. Such assay methods include radioimmunoassays, competitive-binding assays, Western Blot analysis and ELISA assays.

Assaying TR10 protein levels in a biological sample can occur using any art-known method. By "biological sample" is intended any biological sample obtained from an individual, cell line, tissue culture, or other source containing TR10 receptor protein or mRNA. Preferred for assaying TR10 protein levels in a biological sample are antibody-based techniques. For example, TR10 protein expression in tissues can be studied with classical immunohistological methods. (M. Jalkanen et al., *J. Cell. Biol.* 101:976–985 (1985); M. Jalkanen et al., *J. Cell. Biol.* 105:3087–3096 (1987)). Other antibody-bas ed methods useful for detecting TR10 receptor gene express ion include immunoassays, such as the enzyme linked immunosorbent assay (ELISA) and the radioimmunoassay (RIA).

Suitable labels are known in the art and include enzyme labels, such as glucose oxidase, radioisotopes, such as iodine ($^{125}$I, $^{121}$I), carbon ($^{14}$C), sulphur ($^{35}$S), tritium ($^{3}$H), indium ($^{112}$In), and technetium ($^{99m}$Tc), and fluorescent labels, such as fluorescein and rhodamine, and biotin.

Therapeutics

The Tumor Necrosis Factor (TNF) family ligands are known to be among the most pleiotropic cytokines, inducing a large number of cellular responses, including cytotoxicity, anti-viral activity, immunoregulatory activities, and the transcriptional regulation of several genes (D. V. Goeddel et al, "Tumor Necrosis Factors: Gene Structure and Biological Activities," *Symp. Quant. Biol.* 51:597–609 (1986), Cold Spring Harbor; B. Beutler and A. Cerami, *Annu. Rev. Biochem.* 57:505–518 (1988); L. J. Old, *Sci. Am.* 258:59–75 (1988); W. Fiers, *FEBS Lett.* 285:199–224 (1991)). The TNF-family ligands induce such various cellular responses by binding to TNF-family receptors, including the TR10 of the present invention. Cells which express the TR10 polypeptide and are believed to have a potent cellular response to TR10 ligands include fetal liver, PBL, lung, kidney, small intestine, colon, keratinocytes, endothelial cells, and monocyte activated tissue. By "a cellular response to a TNF-family ligand" is intended any genotypic, phenotypic, and/or morphologic change to a cell, cell line, tissue, tissue culture or patient that is induced by a TNF-family ligand. As indicated, such cellular responses include not only normal physiological responses to TNF-family ligands, but also diseases associated with increased apoptosis or the inhibition of apoptosis. Apoptosis-programmed cell death-is a physiological mechanism involved in the deletion of peripheral T lymphocytes of the immune system, and its dysregulation can lead to a number of different pathogenic processes (J. C. Ameisen, *AIDS* 8:1197–1213 (1994); P. H. Krammer et al., *Curr. Opin. Immunol.* 6:279–289 (1994)).

Diseases associated with increased cell survival, or the inhibition of apoptosis, include cancers (such as follicular lymphomas, carcinomas with p53 mutations, and hormone-dependent tumors, such as breast cancer, prostrate cancer, Kaposi's sarcoma and ovarian cancer); autoimmune disorders (such as systemic lupus erythematosus and immune-related glomerulonephritis rheumatoid arthritis); viral infections (such as herpes viruses, pox viruses and adenoviruses); inflammation; graft vs. host disease; acute graft rejection and chronic graft rejection. Diseases associated with increased apoptosis include AIDS; neurodegenerative disorders (such as Alzheimer's disease, Parkinson's disease, Amyotrophic lateral sclerosis, Retinitis pigmentosa, Cerebellar degeneration); myelodysplastic syndromes (such as aplastic anemia), ischemic injury (such as that caused by myocardial infarction, stroke and reperfusion injury), toxin-induced liver disease (such as that caused by alcohol), septic shock, cachexia and anorexia.

Thus, in one aspect, the present invention is directed to a method for enhancing apoptosis induced by a TNF-family ligand, which involves administering to a cell which expresses the TR10 polypeptide an effective amount of TR10 ligand, analog or an agonist capable of increasing TR10 mediated signaling. Preferably, TR10 mediated signaling is increased to treat a disease wherein decreased apoptosis or decreased cytokine and adhesion molecule expression is exhibited. An agonist can include soluble forms of TR10 and monoclonal antibodies directed against the TR10 polypeptide.

In a further aspect, the present invention is directed to a method for inhibiting apoptosis induced by a TNF-family ligand, which involves administering to a cell which expresses the TR10 polypeptide an effective amount of an antagonist capable of decreasing TR10 mediated signaling. Preferably, TR10 mediated signaling is decreased to treat a disease wherein increased apoptosis or NFkB expression is exhibited. An antagonist can include soluble forms of TR10 and monoclonal antibodies directed against the TR10 polypeptide.

By "agonist" is intended naturally occurring and synthetic compounds capable of enhancing or potentiating apoptosis. By "antagonist" is intended naturally occurring and synthetic compounds capable of inhibiting apoptosis. Whether any candidate "agonist" or "antagonist" of the present invention can enhance or inhibit apoptosis can be determined using art-known TNF-family ligand/receptor cellular response assays, including those described in more detail below.

One such screening procedure involves the use of melanophores which are transfected to express the receptor of the present invention. Such a screening technique is described in PCT WO 92/01810, published Feb. 6, 1992. Such an assay may be employed, for example, for screening for a compound which inhibits (or enhances) activation of the receptor polypeptide of the present invention by contacting the melanophore cells which encode the receptor with both a TNF-family ligand and the candidate antagonist (or agonist). Inhibition or enhancement of the signal generated by the ligand indicates that the compound is an antagonist or agonist of the ligand/receptor signaling pathway.

Other screening techniques include the use of cells which express the receptor (for example, transfected CHO cells) in a system which measures extracellular pH changes caused by receptor activation. For example, compounds may be contacted with a cell which expresses the receptor polypeptide of the present invention and a second messenger response, e.g., signal transduction or pH changes, may be measured to determine whether the potential compound activates or inhibits the receptor.

Another such screening technique involves introducing RNA encoding the receptor into Xenopus oocytes to transiently express the receptor. The receptor oocytes may then be contacted with the receptor ligand and a compound to be screened, followed by detection of inhibition or activation of a calcium signal in the case of screening for compounds which are thought to inhibit activation of the receptor.

Another screening technique well known in the art involves expressing in cells a construct wherein the receptor is linked to a phospholipase C or D. Exemplary cells include endothelial cells, smooth muscle cells, embryonic kidney cells, etc. The screening may be accomplished as hereinabove described by detecting activation of the receptor or inhibition of activation of the receptor from the phospholipase signal.

Another method involves screening for compounds which inhibit activation of the receptor polypeptide of the present invention antagonists by determining inhibition of binding of labeled ligand to cells which have the receptor on the surface thereof. Such a method involves transfecting a eukaryotic cell with DNA encoding the receptor such that the cell expresses the receptor on its surface and contacting the cell with a compound in the presence of a labeled form of a known ligand. The ligand can be labeled, e.g., by radioactivity. The amount of labeled ligand bound to the receptors is measured, e.g., by measuring radioactivity of the receptors. If the compound binds to the receptor as determined by a reduction of labeled ligand which binds to the receptors, the binding of labeled ligand to the receptor is inhibited.

Further screening assays for agonists and antagonists of the present invention are described in L. A. Tartaglia and D. V. Goeddel, *J. Biol. Chem.* 267:4304–4307(1992).

Thus, in a further aspect, a screening method is provided for determining whether a candidate agonist or antagonist is capable of enhancing or inhibiting a cellular response to a TNF-family ligand. The method involves contacting cells which express the TR10 polypeptide with a candidate compound and a TNF-family ligand, assaying a cellular response, and comparing the cellular response to a standard cellular response, the standard being assayed when contact is made with the ligand in absence of the candidate compound, whereby an increased cellular response over the standard indicates that the candidate compound is an agonist of the ligand/receptor signaling pathway and a decreased cellular response compared to the standard indicates that the candidate compound is an antagonist of the ligand/receptor signaling pathway. By "assaying a cellular response" is intended qualitatively or quantitatively measuring a cellular response to a candidate compound and/or a TNF-family ligand (e.g., determining or estimating an increase or decrease in T cell proliferation or tritiated thymidine labeling). By the invention, a cell expressing the TR10 polypeptide can be contacted with either an endogenous or exogenously administered TNF-family ligand.

Antagonist according to the present invention include naturally occurring and synthetic compounds such as, for example, TNF family ligand peptide fragments, transforming growth factor, neurotransmitters (such as glutamate, dopamine, N-methyl-D-aspartate), tumor suppressors (p53), cytolytic T cells and antimetabolites. Preferred agonists include chemotherapeutic drugs such as, for example, cisplatin, doxorubicin, bleomycin, cytosine arabinoside, nitrogen mustard, methotrexate and vincristine. Others include ethanol and -amyloid peptide. (*Science* 267:1457–1458 (1995)). Further preferred agonists include polyclonal and monoclonal antibodies raised against the TR10 polypeptide, or a fragment thereof. Such agonist antibodies raised against a TNF-family receptor are disclosed in L. A. Tartaglia et al., *Proc. Natl. Acad. Sci. USA* 88:9292–9296 (1991); and L. A. Tartaglia and D. V. Goeddel, *J. Biol. Chem.* 267:4304–4307(1992). See, also, PCT Application WO 94/09137.

Agonists according to the present invention include naturally occurring and synthetic compounds such as, for example, the CD40 ligand, neutral amino acids, zinc, estrogen, androgens, viral genes (such as Adenovirus E1B, Baculovirus p35 and IAP, Cowpox virus crmA, Epstein-Barr virus BHRF1, LMP-1, African swine fever virus LMW5-HL, and Herpesvirus yl 34.5), calpain inhibitors, cysteine protease inhibitors, and tumor promoters (such as PMA, Phenobarbital, and -Hexachlorocyclohexane).

Other potential antagonists include antisense molecules. Antisense technology can be used to control gene expression through antisense DNA or RNA or through triple-helix formation. Antisense techniques are discussed, for example, in Okano, *J. Neurochem.* 56:560 (1991); *Oligodeoxynucleotides as Antisense Inhibitors of Gene Expression*, CRC Press, Boca Raton, Fla. (1988). Triple helix formation is discussed in, for instance Lee et al., *Nucleic Acids Research* 6:3073 (1979); Cooney et al., *Science* 241:456 (1988); and Dervan et al., *Science* 251:1360 (1991). The methods are based on binding of a polynucleotide to a complementary DNA or RNA.

For example, the 5' coding portion of a polynucleotide that encodes the mature polypeptide of the present invention may be used to design an antisense RNA oligonucleotide of from about 10 to 40 base pairs in length. A DNA oligonucleotide is designed to be complementary to a region of the gene involved in transcription thereby preventing transcription and the production of the receptor. The antisense RNA oligonucleotide hybridizes to the mRNA in vivo and blocks translation of the mRNA molecule into receptor polypeptide. The oligonucleotides described above can also be delivered to cells such that the antisense RNA or DNA may be expressed in vivo to inhibit production of the receptor.

An agonists according to the present invention include soluble forms of TR10, i.e., TR10 fragments that include the ligand binding domain from the extracellular region of the full length receptor. Such soluble forms of the receptor, which may be naturally occurring or synthetic, antagonize TR10 mediated signaling by competing with the cell surface TR10 for binding to TNF-family ligands. However, soluble TR10 may bind to apoptosis inducing ligands such as TRAIL and more effectively compete for TRAIL binding reducing the available TRAIL for binding to receptors with functional death domains. Thus, soluble forms of the receptor that include the ligand binding domain are novel cytokines capable of inhibiting apoptosis induced by TNF-family ligands. These are preferably expressed as dimers or trimers, since these have been shown to be superior to monomeric forms of soluble receptor as antagonists, e.g., IgGFc-TNF receptor family fusions. Other such cytokines are known in the art and include Fas B (a soluble form of the mouse Fas receptor) that acts physiologically to limit apoptosis induced by Fas ligand (D. P. Hughes and I. N. Crispe, *J. Exp. Med.* 182:1395–1401 (1995)).

The term "antibody" (Ab) or "monoclonal antibody" (mAb) as used herein is meant to include intact molecules as well as fragments thereof (such as, e.g., Fab and F(ab')$_2$ fragments) which are capable of binding an antigen. Fab and F(ab')$_2$ fragments lack the Fc fragment of intact antibody, clear more rapidly from the circulation, and may have less non-specific tissue binding of an intact antibody (Wahl et al., *J. Nucl. Med.* 24:316–325 (1983)).

Antibodies according to the present invention may be prepared by any of a variety of methods using TR10 immunogens of the present invention. As indicated, such TR10 immunogens include the full length TR10 polypeptide (which may or may not include the leader sequence) and TR10 polypeptide fragments such as the ligand binding domain, the transmembrane domain, the intracellular domain and the incomplete death domain.

Proteins and other compounds which bind the TR10 domains are also candidate agonists and antagonists according to the present invention. Such binding compounds can be "captured" using the yeast two-hybrid system (Fields and Song, *Nature* 340:245–246 (1989)). A modified version of the yeast two-hybrid system has been described by Roger Brent and his colleagues (J. Gyuris, *Cell* 75:791–803 (1993); A. S. Zervos et al., *Cell* 72:223–232 (1993)). Preferably, the yeast two-hybrid system is used according to the present invention to capture compounds which bind to either the TR10 ligand binding domain or to the TR10 intracellular domain. Such compounds are good candidate agonists and antagonists of the present invention.

By a "TNF-family ligand" is intended naturally occurring, recombinant, and synthetic ligands that are capable of binding to a member of the TNF receptor family and inducing the ligand/receptor signaling pathway. Members of the TNF ligand family include, but are not limited to TR10 ligands including TRAIL, TNF-α, lymphotoxin-α (LT-α, also known as TNF-β), LT-β (found in complex heterotrimer LT-α2-β), FasL, CD40, CD27, CD30, 4-1BB, OX40, and nerve growth factor (NGF).

Representative therapeutic applications of the present invention are discussed in-more detail below. The state of immunodeficiency that defines AIDS is secondary to a decrease in the number and function of $CD4^+$ T-lymphocytes. Recent reports estimate the daily loss of $CD4^+$ T cells to be between $3.5 \times 10^7$ and $2 \times 10^9$ cells (X. Wei et al., Nature 373:117–122 (1995)). One cause of $CD4^+$ T cell depletion in the setting of HIV infection is believed to be HIV-induced apoptosis. Indeed, HIV-induced apoptotic cell death has been demonstrated not only in vitro but also, more importantly, in infected individuals (J. C. Ameisen, AIDS 8:1197–1213 (1994); T. H. Finkel and N. K. Banda, Curr. Opin. Immunol. 6:605–615(1995); C. A. Muro-Cacho et al., J. Immunol. 154:5555–5566 (1995)). Furthermore, apoptosis and $CD4^+$ T-lymphocyte depletion is tightly correlated in different animal models of AIDS (T. Brunner et al., Nature 373:441–444 (1995); M. L. Gougeon et al., AIDS Res. Hum. Retroviruses 9:553–563 (1993)) and, apoptosis is not observed in those animal models in which viral replication does not result in AIDS. Id. Further data indicates that uninfected but primed or activated T lymphocytes from HIV-infected individuals undergo apoptosis after encountering the TNF-family ligand FasL. Using monocytic cell lines that result in death following HIV infection, it has been demonstrated that infection of U937 cells with HIV results in the de novo expression of FasL and that FasL mediates HIV-induced apoptosis (A. D. Badley et al., J. Virol. 70:199–206 (1996)). Further, the TNF-family ligand was detectable in uninfected macrophages and its expression was upregulated following HIV infection resulting in selective killing of uninfected CD4 T-lymphocytes. Id. Thus, by the invention, a method for treating $HIV^+$ individuals is provided which involves administering an antagonist of the present invention to reduce selective killing of CD4 T-lymphocytes. Modes of administration and dosages are discussed in detail below.

In rejection of an allograft, the immune system of the recipient animal has not previously been primed to respond because the immune system for the most part is only primed by environmental antigens. Tissues from other members of the same species have not been presented in the same way that, for example, viruses and bacteria have been presented. In the case of allograft rejection, immunosuppressive regimens are designed to prevent the immune system from reaching the effector stage. However, the immune profile of xenograft rejection may resemble disease recurrence more that allograft rejection. In the case of disease recurrence, the immune system has already been activated, as evidenced by destruction of the native islet cells. Therefore, in disease recurrence, the immune system is already at the effector stage. Antagonists of the present invention are able to suppress the immune response to both allografts and xenografts because lymphocytes activated and differentiated into effector cells will express the TR10 polypeptide, and thereby are susceptible to compounds which enhance apoptosis. Thus, the present invention further provides a method for creating immune privileged tissues.

TR10 antagonists of the invention can further be used in the treatment of inflammatory diseases, such as inflammatory bowel disease, rheumatoid arthritis, osteoarthritis, psoriasis, and septicemia.

In addition, due to lymphoblast expression of TR10, soluble TR10 agonist or antagonist mABs may be used to treat this form of cancer.

Modes of Administration

The agonist or antagonists described herein can be administered in vitro, ex vivo, or in vivo to cells which express the receptor of the present invention. By administration of an "effective amount" of an agonist or antagonist is intended an amount of the compound that is sufficient to enhance or inhibit a cellular response to a TNF-family ligand and include polypeptides. In particular, by administration of an "effective amount" of an agonist or antagonists is intended an amount effective to enhance or inhibit TR10 mediated apoptosis. Of course, where it is desired for apoptosis to be enhanced, an agonist according to the present invention can be co-administered with a TNF-family ligand. One of ordinary skill will appreciate that effective amounts of an agonist or antagonist can be determined empirically and may be employed in pure form or in pharmaceutically acceptable salt, ester or prodrug form. The agonist or antagonist may be administered in compositions in combination with one or more pharmaceutically acceptable excipients.

It will be understood that, when administered to a human patient, the total daily usage of the compounds and compositions of the present invention will be decided by the attending physician within the scope of sound medical judgment. The specific therapeutically effective dose level for any particular patient will depend upon factors well known in the medical arts.

As a general proposition, the total pharmaceutically effective amount of TR10 polypeptide administered parenterally per dose will be in the range of about 1 g/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day for the hormone. If given continuously, the TR10 polypeptide is typically administered at a dose rate of about 1 g/kg/hour to about 50 g/kg/hour, either by 1–4 injections per day or by continuous subcutaneous infusions, for example, using a mini-pump. An intravenous bag solution may also be employed.

Dosaging may also be arranged in a patient specific manner to provide a predetermined concentration of an agonist or antagonist in the blood, as determined by the RIA technique. Thus patient dosaging may be adjusted to achieve regular on-going trough blood levels, as measured by RIA, on the order of from 50 to 1000 ng/ml, preferably 150 to 500 ng/ml.

Pharmaceutical compositions containing the TR10 polypeptide of the invention may be administered orally, rectally, parenterally, intracistemally, intravaginally, intraperitoneally, topically (as by powders, ointments, drops or transdermal patch), bucally, or as an oral or nasal spray. By "pharmaceutically acceptable carrier" is meant a non-toxic solid, semisolid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

Pharmaceutical compositions of the present invention for parenteral injection can comprise pharmaceutically acceptable sterile aqueous or nonaqueous solutions, dispersions, suspensions or emulsions as well as sterile powders for reconstitution into sterile injectable solutions or dispersions just prior to use.

In addition to soluble TR10 polypeptides, TR10 polypeptides containing the transmembrane region can also be used when appropriately solubilized by including detergents, such as CHAPS or NP-40, with buffer.

Chromosome Assays

The nucleic acid molecules of the present invention are also valuable for chromosome identification. The sequence is specifically targeted to and can hybridize with a particular location on an individual human chromosome. The mapping of DNAs to chromosomes according to the present invention is an important first step in correlating those sequences with genes associated with disease.

In certain preferred embodiments in this regard, the cDNA herein disclosed is used to clone genomic DNA of a TR10 receptor gene. This can be accomplished using a variety of well known techniques and libraries, which generally are available commercially. The genomic DNA is then used for in situ chromosome mapping using well known techniques for this purpose.

In addition, in some cases, sequences can be mapped to chromosomes by preparing PCR primers (preferably 15–25 bp) from the cDNA. Computer analysis of the 3' untranslated region of the gene is used to rapidly select primers that do not span more than one exon in the genomic DNA, thus complicating the amplification process. These primers are then used for PCR screening of somatic cell hybrids containing individual human chromosomes.

Fluorescence in situ hybridization ("FISH") of a cDNA clone to a metaphase chromosomal spread can be used to provide a precise chromosomal location in one step. This technique can be used with cDNA as short as 50 or 60 bp. For a review of this technique, see Verma et al., *Human Chromosomes: a Manual of Basic Techniques*, Pergamon Press, New York (1988).

Once a sequence has been mapped to a precise chromosomal location, the physical position of the sequence on the chromosome can be correlated with genetic map data. Such data are found, for example, in V. McKusick, *Mendelian Inheritance in Man*, available on line through Johns Hopkins University, Welch Medical Library. The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

Having generally described the invention, the same will be more readily understood by reference to the following examples, which are provided by way of illustration and are not intended as limiting.

EXAMPLE 1

Expression and Purification of the TR10 Receptor in *E. coli*

The bacterial expression vector pQE60 is used for bacterial expression in this example. (QIAGEN, Inc., 9259 Eton Avenue, Chatsworth, Calif., 91311). pQE60 encodes ampicillin antibiotic resistance ("Amp$^r$") and contains a bacterial origin of replication ("ori"), an IPTG inducible promoter, a ribosome binding site ("RBS"), six codons encoding histidine residues that allow affinity purification using nickel-nitrilo-tri-acetic acid ("Ni-NTA") affinity resin sold by QIAGEN, Inc., supra, and suitable single restriction enzyme cleavage sites. These elements are arranged such that a DNA fragment encoding a polypeptide may be inserted in such as way as to produce that polypeptide with the six His residues (i.e., a "6×His tag") covalently linked to the carboxyl terminus of that polypeptide. However, in this example, the polypeptide coding sequence is inserted such that translation of the six His codons is prevented and, therefore, the polypeptide is produced with no 6×His tag.

The DNA sequence encoding the desired portion of the TR10 protein lacking the hydrophobic leader sequence is amplified from the deposited cDNA clone using PCR oligonucleotide primers which anneal to the amino terminal sequences of the desired portion of the TR10 protein and to sequences in the deposited construct 3'to the cDNA coding sequence. Additional nucleotides containing restriction sites to facilitate cloning in the pQE60 vector are added to the 5' and 3' sequences, respectively.

For cloning the mature protein, the 5' primer has the sequence: 5'-CGCCCATGGCCACCATCCCCCGGCAG-3' (SEQ ID NO: 10) containing the underlined NcoI restriction site followed by nucleotides complementary to the amino terminal coding sequence of the mature TR10 sequence in FIGS. 1A–F. One of ordinary skill in the art would appreciate, of course, that the point in the protein coding sequence where the 5' primer begins may be varied to amplify a desired portion of the complete protein shorter or longer than the mature form.

The 3' primer has the sequence: 5'-CGCAAGCTTTTAGTAGTGATAGGGAGAGGC-3' (SEQ ID NO:11) containing the underlined HindIII site followed by nucleotides complementary to the 3' end of the non-coding sequence in the TR10 DNA sequence in FIGS. 1A–F.

The amplified TR10 DNA fragments and the vector pQE60 are digested with Nco I and HindIII and the digested DNAs then ligated together. Insertion of the TR10 protein DNA into the restricted pQE60 vector places the TR10 protein coding region (including its associated stop codon) downstream from the IPTG-inducible promoter and in-frame with an initiating AUG. The associated stop codon prevents translation of the six histidine codons downstream of the insertion point.

The ligation mixture is transformed into competent *E. coli* cells using standard procedures. Such procedures are described in Sambrook et al., *Molecular Cloning: a Laboratory Manual*, 2nd Ed.; Cold Spring Harbor Laboratory Press, Cold Spring Harbor, N.Y. (1989). *E. coli* strain M15/rep4, containing multiple copies of the plasmid pREP4, which expresses lac repressor and confers kanamycin resistance ("Kan$^r$"), is used in carrying out the illustrative example described herein. This strain, which is only one of many that are suitable for expressing TR10 protein, is available commercially from Qiagen, Inc., supra.

Transformants are identified by their ability to grow on LB plates in the presence of ampicillin and kanamycin. Plasmid DNA is isolated from resistant colonies and the identity of the cloned DNA confirmed by restriction analysis, PCR, and DNA sequencing.

Clones containing the desired constructs are grown overnight ("O/N") in liquid culture in LB media supplemented with both ampicillin (100 µg/ml) and kanamycin (25 µg/ml).

The O/N culture is used to inoculate a large culture, at a dilution of approximately 1:100 to 1:250. The cells are grown to an optical density at 600 nm ("OD600") of between 0.4 and 0.6. Isopropyl-B-D-thiogalactopyranoside ("IPTG") is then added to a final concentration of 1 mM to induce transcription from the lac repressor sensitive promoter, by inactivating the lacI repressor. Cells subsequently are incubated further for 3 to 4 hours. Cells then are harvested by centrifugation.

The cells are then stirred for 3–4 hours at 4° C. in 6M guanidine-HCl, pH8. The cell debris is removed by centrifugation, and the supernatant containing the TR10 is loaded onto a nickel-nitrilo-tri-acetic acid ("NiNTA") affinity resin column (available from QIAGEN, Inc., supra). Proteins with a 6×His tag bind to the NI-NTA resin with high affinity and can be purified in a simple one-step procedure (for details see: The QIAexpressionist, 1995, QIAGEN, Inc., supra). Briefly the supernatant is loaded onto the column in 6 M guanidine-HCl, pH8, the column is first washed with 10 volumes of 6 M guanidine-HCl, pH8, then washed with 10 volumes of 6 M guanidine-HCl pH6, and finally the TR10 is eluted with 6 M guanidine-HCl, pH5.

The purified protein is then renatured by dialyzing it against phosphatebuffered saline (PBS) or 50 mM Na-acetate, pH 6 buffer plus 200 mM NaCl. Alternatively, the protein can be successfully refolded while immobilized on the Ni-NTA column. The recommended conditions are as follows: renature using a linear 6M–1M urea gradient in 500 mM NaCl, 20% glycerol, 20 mM Tris/HCl pH7.4, containing protease inhibitors. The renaturation should be performed over a period of 1.5 hours or more. After renaturation the proteins can be eluted by the addition of 250 mM immidazole. Immidazole is removed by a final dialyzing step against PBS or 50 mM sodium acetate pH6 buffer plus 200 mM NaCl. The purified protein is stored at 4° C. or frozen at −80° C.

EXAMPLE 2

Cloning and Expression of TR10 in a Baculovirus Expression System

In this illustrative example, the plasmid shuttle vector pA2 is used to insert the cloned DNA encoding the complete protein, including its naturally associated secretary signal (leader) sequence, into a baculovirus to express the mature TR10 protein, using standard methods as described in Summers et al., *A Manual of Methods for Baculovirus Vectors and Insect Cell Culture Procedures*, Texas Agricultural Experimental Station Bulletin No. 1555 (1987). This expression vector contains the strong polyhedrin promoter of the *Autographa californica* nuclear polyhedrosis virus (AcMNPV) followed by convenient restriction sites such as BamHI and Asp718. The polyadenylation site of the simian virus 40 ("SV40") is used for efficient polyadenylation. For easy selection of recombinant virus, the plasmid contains the beta-galactosidase gene from *E. coli* under control of a weak Drosophila promoter in the same orientation, followed by the polyadenylation signal of the polyhedrin gene. The inserted genes are flanked on both sides by viral sequences for cell-mediated homologous recombination with wild-type viral DNA to generate viable virus that express the cloned polynucleotide.

Many other baculovirus vectors could be used in place of the vector above, such as pAc373, pVL941 and pAcIM1, as one skilled in the art would readily appreciate, as long as the construct provides appropriately located signals for transcription, translation, secretion and the like, including a signal peptide and an in-frame AUG as required. Such vectors are described, for instance, in Luckow et al., *Virology* 170:31–39 (1989).

The cDNA sequence encoding the mature TR10 receptor protein in the deposited clone, lacking the AUG initiation codon and the naturally associated leader sequence shown in FIGS. 1A–F (SEQ ID NO:2), is amplified using PCR oligonucleotide primers corresponding to the 5' and 3' sequences of the gene.

The 5' primer has the sequence 5' CGCGGATCC GCCAT-CATGGGACTTTGGGGACAA 3' (SEQ ID NO:12) containing the underlined BamHI restriction enzyme site, an efficient signal for initiation of translation in eukaryotic cells, as described by M. Kozak, *J. Mol. Biol.* 196:947–950 (1987), followed by bases of the sequence of the mature TR10 protein shown in FIGS. 1A–F, beginning with the indicated N-terminus of the mature protein.

The 3' primer for TR10 has the sequence 5' CGCGG-TACCTTAGTAGTGATAGGGAGAGGC 3' (SEQ ID NO:13) containing the underlined Asp718 restriction site followed by nucleotides complementary to the 3' noncoding sequence in FIGS. 1A–F.

The amplified fragment is isolated from a 1% agarose gel using a commercially available kit ("Geneclean," BIO 101 Inc., La Jolla, Calif.) The fragment then is digested with BamHI and Asp718 and again is purified on a 1% agarose gel. This fragment is designated "F1."

The plasmid is digested with the restriction enzyme Bam HI and optionally can be dephosphorylated using calf intestinal phosphatase, using routine procedures known in the art. The DNA is then isolated from a 1% agarose gel using a commercially available kit ("Geneclean" BIO 101 Inc., La Jolla, Calif.). The vector DNA is designated herein "V1."

Fragment F1 and the dephosphorylated plasmid V1 are ligated together with T4 DNA ligase. *E. coli* HB 101 or other suitable *E. coli* hosts such as XL-1 Blue (Stratagene Cloning Systems, La Jolla, Calif.) cells are transformed with the ligation mixture and spread on culture plates. Bacteria are identified that contain the plasmid with the human TR10 gene using the PCR method, in which one of the primers that is used to amplify the gene and the second primer is from well within the vector so that only those bacterial colonies containing the TR10 gene fragment will show amplification of the DNA. The sequence of the cloned fragment is confirmed by DNA sequencing. This plasmid is designated herein pBacTR10.

Five μg of the plasmid pBacTR10 is co-transfected with 1.0 μg of a commercially available linearized baculovirus DNA ("BaculoGold™ baculovirus DNA", Pharmingen, San Diego, Calif.), using the lipofectin method described by Felgner et al., *Proc. Natl. Acad. Sci. USA* 84:7413–7417 (1987). 1 mg of BaculoGold™ virus DNA and 5 μg of the plasmid pBacTR10 are mixed in a sterile well of a microliter plate containing 50 ml of serum free Grace's medium (Life Technologies, Inc., Rockville, Md.). Afterwards, 10 μl Lipofectin plus 90 μl Grace's medium are added, mixed, and incubated for 15 minutes at room temperature. Then, the transfection mixture is added drop-wise to Sf9 insect cells (ATCC CRL 1711) seeded in a 35 mm tissue culture plate with 1 ml Grace's medium without serum. The plate is rocked back and forth to mix the newly added solution. The plate is then incubated for 5 hours at 27° C. After 5 hours, the transfection solution is removed from the plate and 1 ml of Grace's insect medium supplemented with 10% fetal calf serum is added. The plate is put back into an incubator and cultivation is continued at 27° C. for four days.

After four days, the supernatant is collected and a plaque assay is performed, as described by Summers and Smith, cited above. An agarose gel with "Blue Gal" (Life Technologies, Inc., Rockville, Md.) is used to allow easy identification and isolation of gal-expressing clones, which produce blue-stained plaques. (A detailed description of a "plaque assay" of this type can also be found in the user's guide for insect cell culture and baculovirology distributed by Life Technologies, Inc., Rockville, Md., pages 9–10). After appropriate incubation, blue stained plaques are picked with the tip of a micropipettor (e.g., Eppendorf). The agar containing the recombinant viruses is then resuspended in a microcentrifuge tube containing 200 µl of Grace's medium and the suspension containing the recombinant baculovirus is used to infect Sf9 cells seeded in 35 mm dishes. Four days later the supernatants of these culture dishes are harvested and then they are stored at 4° C. The recombinant virus is called V-TR10.

To verify the expression of the TR10 gene, Sf9 cells are grown in Grace's medium supplemented with 10% heat inactivated FBS. The cells are infected with the recombinant baculovirus V-TR10 at a multiplicity of infection ("MOI") of about 2. Six hours later the medium is removed and is replaced with SF900 II medium minus methionine and cysteine (available from Life Technologies, Inc., Rockville, Md.). If radiolabeled proteins are desired, 42 hours later, 5 µCi of $^{35}$S. methionine and 5 µCi $^{35}$S. cysteine (available from Amersham) are added. The cells are further incubated for 16 hours and then they are harvested by centrifugation. The proteins in the supernatant as well as the intracellular proteins are analyzed by SDS-PAGE followed by autoradiography (if radiolabeled). Microsequencing of the amino acid sequence of the amino terminus of purified protein may be used to determine the amino terminal sequence of the mature protein and thus the cleavage point and length of the secretory signal peptide.

EXAMPLE 3

Cloning and Expression of the TR10 Receptor in Mammalian Cells

A typical mammalian expression vector contains the promoter element, which mediates the initiation of transcription of mRNA, the protein coding sequence, and signals required for the termination of transcription and polyadenylation of the transcript. Additional elements include enhancers, Kozak sequences and intervening sequences flanked by donor and acceptor sites for RNA splicing. Highly efficient transcription can be achieved with the early and late promoters from SV40, the long terminal repeats (LTRs) from Retroviruses, e.g. RSV, HTLVI, HIVI and the early promoter of the cytomegalovirus (CMV). However, cellular signals can also be used (e.g., the human actin promoter). Suitable expression vectors for use in practicing the present invention include, for example, vectors such as pSVL and pMSG (Pharmacia, Uppsala, Sweden), pRSVcat (ATCC 37152), pSV2dhfr (ATCC 37146) and pBC12MI (ATCC 67109). Mammalian host cells that could be used include, human Hela 293, H9 and Jurkat cells, mouse NIH3T3 and C127 cells, Cos 1, Cos 7 and CV1, quail QC1-3 cells, mouse L cells, and Chinese hamster ovary (CHO) cells.

Alternatively, the gene can be expressed in stable cell lines that contain the gene integrated into a chromosome. Co-transfection with a selectable marker such as dhfr, gpt, neomycin, or hygromycin allows the identification and isolation of the transfected cells.

The transfected gene can also be amplified to express large amounts of the encoded protein. The dihydrofolate reductase (DHFR) marker is useful to develop cell lines that carry several hundred or even several thousand copies of the gene of interest. Another useful selection marker is the enzyme glutamine synthase (GS) (Murphy et al., *Biochem. J.* 227:277–279 (1991); Bebbington et al., *Bio/Technology* 10:169–175 (1992)). Using these markers, the mammalian cells are grown in selective medium and the cells with the highest resistance selected. These cell lines contain the amplified gene(s) integrated into a chromosome. Chinese hamster ovary (CHO) cells are often used for the production of proteins.

The expression vectors pC1 and pC4 contain the strong promoter (LTR) of the Rous Sarcoma Virus (Cullen et al., *Molecular and Cellular Biology* 5:438–447 (March 1985)), plus a fragment of the CMV-enhancer (Boshart et al., *Cell* 41:521–530 (1985)). Multiple cloning sites, e.g., with the restriction enzyme cleavage sites BamHI, XbaI and Asp718, facilitate the cloning of the gene of interest. The vectors contain in addition the 3' intron, the polyadenylation and termination signal of the rat preproinsulin gene.

EXAMPLE 3A

Cloning and Expression of the Extracellular Soluble Domain of TR10 in COS cells

The expression plasmid, pTR10-HA, is made by cloning a cDNA encoding TR10 into the expression vector pcDNAI/Amp or pcDNAIII (which can be obtained from Invitrogen, Inc.).

The expression vector pcDNAI/amp contains: (1) an *E. coli* origin of replication effective for propagation in *E. coli* and other prokaryotic cell; (2) an ampicillin resistance gene for selection of plasmid-containing prokaryotic cells; (3) an SV40 origin of replication for propagation in eukaryotic cells; (4) a CMV promoter, a polylinker, an SV40 intron, and a polyadenylation signal arranged so that a cDNA conveniently can be placed under expression control of the CMV promoter and operably linked to the SV40 intron and the polyadenylation signal by means of restriction sites in the polylinker.

A DNA fragment encoding the entire TR10 precursor and a HA tag fused in frame to its 3' end is cloned into the polylinker region of the vector so that recombinant protein expression is directed by the CMV promoter. The HA tag corresponds to an epitope derived from the influenza hemagglutinin protein described by Wilson et al., *Cell* 37:767 (1984). The fusion of the HA tag to the target protein allows easy detection of the recombinant protein with an antibody that recognizes the HA epitope.

The plasmid construction strategy is as follows:

The TR10 cDNA of the deposited clone is amplified using primers that contain convenient restriction sites, much as described above regarding the construction of expression vectors for expression of TR10 in *E. coli*.

To facilitate detection, purification and characterization of the expressed TR10, one of the primers contains a hemagglutinin tag ("HA tag") as described above.

Suitable primers for TR10 include the following, which are used in this example:

The 5' primer, 5' CGCGGATCCGCCATCATGG-GACTTTGGGGACAA 3' (SEQ ID NO:12) contains the underlined BamHI site, an ATG start codon and 5 codons thereafter. The 3' primer for TR10, which contains the underlined XbaI site, stop codon, hemagglutinin tag, and the last 19 nucleotides of the 3' coding sequence (at the 3' end), has the following sequence: 5' CGCTCTAGATCAAGCG-TAGTCTGGGACGTCGTATGGGTAGTAAGT GATAGG-GAGAGGC 3' (SEQ ID NO:14).

The PCR amplified DNA fragment and the vector, pcDNAI/Amp, are digested with BamHI and XbaI and then ligated. The ligation mixture is transformed into E. coli strain SURE (available from Stratagene Cloning Systems, 11099 North Torrey Pines Road, La Jolla, Calif. 92037) the transformed culture is plated on ampicillin media plates which then are incubated to allow growth of ampicillin resistant colonies. Plasmid DNA is isolated from resistant colonies and examined by restriction analysis and gel sizing for the presence of the TR10-encoding fragment.

For expression of recombinant TR10, COS cells are transfected with an expression vector, as described above, using DEAE-DEXTRAN, as described, for instance, in Sambrook et al., *Molecular Cloning: a Laboratory Manual*, Cold Spring Laboratory Press, Cold Spring Harbor, N.Y. (1989). Cells are incubated under conditions for expression of TR10 by the vector.

Expression of the TR10-HA fusion protein is detected by radiolabelling and immunoprecipitation, using methods described in, for example Harlow et al., *Antibodies: a Laboratory Manual,* 2nd Ed., Cold Spring Harbor Laboratory Press, Cold Spring Harbor, N.Y. (1988). To this end, two days after transfection, the cells are labeled by incubation in media containing $^{35}$S-cysteine for 8 hours. The cells and the media are collected, and the cells are washed and then lysed with detergent-containing RIPA buffer: 150 mM NaCl, 1% NP-40, 0.1% SDS, 1% NP-40, 0.5% DOC, 50 mM TRIS, pH 7.5, as described by Wilson et al. cited above. Proteins are precipitated from the cell lysate and from the culture media using an HA-specific monoclonal antibody. The precipitated proteins then are analyzed by SDS-PAGE gels and autoradiography. An expression product of the expected size is seen in the cell lysate, which is not seen in negative controls.

EXAMPLE 3B

Cloning and Expression of TR10 using the CHO Expression System

The vector pC4 is used for the expression of the TR10 polypeptide. Plasmid pC4 is a derivative of the plasmid pSV2-dhfr (ATCC Accession No. 37146). The plasmid contains the mouse DHFR gene under control of the SV40 early promoter. Chinese hamster ovary- or other cells lacking dihydrofolate activity that are transfected with these plasmids can be selected by growing the cells in a selective medium (alpha minus MEM, Life Technologies, Rockville, Md.) supplemented with the chemotherapeutic agent methotrexate (MTX). The amplification of the DHFR genes in cells resistant to MTX has been well documented (see, e.g., F. W. Alt et al., *J. Biol. Chem.* 253:1357–1370 (1978); J. L. Hamlin and C. Ma, *Biochem. et Biophys. Acta* 1097:107–143 (1990); M. J. Page M. A. Sydenham, *Biotechnology* 9:64–68(1991)). Cells grown in increasing concentrations of MTX develop resistance to the drug by overproducing the target enzyme, DHFR, as a result of amplification of the DHFR gene. If a second gene is linked to the DHFR gene, it is usually co-amplified and overexpressed. It is known in the art that this approach may be used to develop cell lines carrying more than 1,000 copies of the amplified gene(s). Subsequently, when the methotrexate is withdrawn, cell lines are obtained that contain the amplified gene integrated into one or more chromosome(s) of the host cell.

Plasmid pC4 contains, for expressing the gene of interest, the strong promoter of the long terminal repeat (LTR) of the Rous Sarcoma Virus (Cullen et al., *Molecular and Cellular Biology* 5:438–447 (March 1985)), plus a fragment isolated from the enhancer of the immediate early gene of human cytomegalovirus (CMV) (Boshart et al., *Cell* 41:521–530 (1985)). Downstream of the promoter are the following single restriction enzyme cleavage sites that allow the integration of the genes: BamHI, XbaI, and Asp718. Behind these cloning sites, the plasmid contains the 3' intron and the polyadenylation site of the rat preproinsulin gene. Other high efficiency promoters can also be used for the expression, e.g., the human B-actin promoter, the SV40 early or late promoters or the long terminal repeats from other retroviruses, e.g., HIV and HTLVI. Clontech's Tet-Off and Tet-On gene expression systems and similar systems can be used to express the TR10 polypeptide in a regulated way in mammalian cells. For the polyadenylation of the mRNA, other signals, e.g., from the human growth hormone or globin genes, can be used as well.

Stable cell lines carrying a gene of interest integrated into the chromosomes can also be selected upon co-transfection with a selectable marker such as gpt, G418, or hygromycin. It is advantageous to use more than one selectable marker in the beginning, e.g., G418 plus methotrexate.

The plasmid pC4 is digested with the restriction enzyme BamHI and then dephosphorylated using calf intestinal phosphates, by procedures known in the art. The vector is then isolated from a 1% agarose gel.

The DNA sequence encoding the complete TR10 polypeptide is amplified using PCR oligonucleotide primers corresponding to the 5' and 3' sequences of the desired portion of the gene.

The 5' oligonucleotide primer for TR10, containing the underlined BamHI Restriction site, a Kozak sequence, and an AUG start codon, has the sequence: 5' CGC GGATCCGCCATCATGGGACTTTGGGGACAA 3' (SEQ ID NO:12). The 3' primer for TR10, containing the underlined Asp718 restriction site, has the sequence: 5' CGC GGTACCTTAGTAGTGATAGGGAGAGGC 3' (SEQ ID NO:13).

The amplified fragment is digested with BamHI and then purified again on a 1% agarose gel. The isolated fragment and the dephosphorylated vector are then ligated with T4 DNA ligase. *E. coli* HB101 or XL-1 Blue cells are then transformed and bacteria are identified that contain the fragment inserted into plasmid pC4 using, for instance, restriction enzyme analysis.

Chinese hamster ovary cells lacking an active DHFR enzyme are used for transfection. Five µg of the expression plasmid pC4 are contransfected with 0.5 µg of the plasmid pSVneo using the lipofectin method (Felgner et al., supra). The plasmid pSV2-neo contains a dominant selectable marker, the neo gene from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) in alpha minus MEM supplemented with 10, 25, or 50 ng/ml of MTX plus 1 mg/ml G418. After about 10–14 days, single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 μM, 2 μM, 5 μM, 10 μM, 20 μM). The same procedure is repeated until clones are obtained which grow at a concentration of 100–200 μM. Expression of the desired gene product is analyzed, for instance, by Western blot analysis and SDS-PAGE, or by reversed phase HPLC analysis.

EXAMPLE 4

Tissue Distribution of TR10 mRNA Expression

Northern blot analysis was carried out to examine TR10 gene expression in human tissues, using methods described by, among others, Sambrook et al., cited above. A cDNA probe containing the entire nucleotide sequence of the TR10 protein (SEQ ID NO:1) was labeled with $^{32}$P using the rediprime™ DNA labeling system (Amersham Life Science), according to manufacturer's instructions. After labeling, the probe was purified using a CHROMA SPIN-100 column (Clontech Laboratories, Inc.), according to manufacturer's protocol number PT1200-1. The purified labeled probe was then used to examine various human tissues for TR10 mRNA.

Multiple Tissue Northern (MTN) blots containing various human tissues (H) or human immune system tissues (IM) were obtained from Clontech and were examined with labeled probe using ExpressHyb™ hybridization solution (Clontech) according to manufacturer's protocol number PT 1190-1. Following hybridization and washing, the blots were mounted and exposed to film at −70° C. overnight, and films developed according to standard procedures. Expression of TR10 was detected in tissues enriched in lymphocytes including peripheral blood leukocytes (PBLs), fetal liver, lung, kidney, small intestine, colon, keratinocytes, endothelial cells, and monocyte activated tissue. It can be envisaged that TR10 plays a role in lymphocyte homeostasis.

Northern Blot Analysis of TR10 in Various Cell Lines
Methods
    Cells

Unless stated otherwise, cell lines were obtained from the American Type Culture Collection (Manassas, Va.). The myeloid (Koeffler et al. (1980); Koeffler (1983); Harris and Ralph (1985); and Tucker et al. (1987) and B-cell lines (Jonak et al. (1922)) studied represent cell types at different stages of the differentiation pathway. KG1a and PLB 985 cells (Tucker et al. (1987)) were obtained from H. P. Koeffler (UCLA School of Medicine). BJA-B was from Z. Jonak (SmithKline Beecham). TF274, a stromal cell line exhibiting osteoblastic features, was generated from the bone marrow of a healthy male donor (Z. Jonak and K. B. Tan, unpublished). Primary carotid artery endothelial cells were purchased from Clonetics Corp. (San Diego, Calif.) and monocytes were prepared by differential centrifugation of peripheral blood mononuclear cells and adhesion to tissue culture dish. CD19+, CD4+ and CD8+ cells (>90% pure) were isolated with cell type specific immunomagnetic beads (Drynal, Lake Success, N.Y.).

RNA Analysis

Total RNA of adult tissues were purchased from Clonetech (Palo Alto, Calif.). Total RNA was extracted from cell lines (in exponential growth phase) and primary cells with TriReagent (Molecular Research Center, Inc., Cincinnati, Ohio). 5 to 7.5 μg of total RNA was fractionated in a 1% agarose gel containing formaldehyde cast in a Wide Mini-Sub Cell gel tray (Bio-Rad, Hercules, Calif.) as described (Sambrook, et al.) with slight modifications. The formaldehyde concentration was reduced to 0.5M and the RNA was stained prior to electrophoresis with 100 μg/ml of ethidium bromide that was added to the loading buffer. After electrophoresis with continuous buffer recirculation (60 volts/90 min), the gel was photographed and the RNA was transferred quantitatively to Zeta-probe nylon membrane (Biorad, Hercules, Calif.) by vacuum-blotting with 25 mM NaOH for 90 min. After neutralization for 5–10 min, with 1M Tris-HCl, pH 7.5 containing 3M NaCl, the blots were prehybridized with 50% formamide, 8% dextran sulfate, 6×SSPE, 0.1% SDS and 100 g/ml of sheared and denatured salmon sperm DNA for at least 30 min at 42° C. cDNA inserts labeled with $^{32}$P-dCTP by random priming (Stratagene, La Jolla, Calif.), were denatured with 0.25M NaOH (10 min at 37° C.) and added to the prehybridization solution. After 24–65 hr at 42° C., the blots were washed under high stringency conditions (Sambrook, et al.) and exposed to X-ray films.

Results

Expression of TR10 was assessed by Northern blot in the following cell lines: HL60 (promyelocytic leukemia), Hela cell S3, K562 (chronic myelogeneous leukemia), MOLT4 (lymphoblast leukemia), Raji (Burkitt's lymphoma), SW480 (colorectal adenocarcinoma), A549 (lung carcinoma), and G361 (melanoma), and could only be detected in Hela cell S3, SW480 (colorectal adenocarcinoma), and the A549 (lung carcinoma) cell lines.

EXAMPLE 5

TR10 Induced Apoptosis

Since the entire sequence of TR10, especially its extracelular cysteine-rich domains, is highly homologous to that of other TRAIL receptors, the ability to TRAIL to bind TR10 and induce apoptosis was assessed.
Experimental Design To facilitate detection, TR10 (amino acids 56–386) was cloned into pCMV2FLAG (IBI Kodak) as an in-frame fusion to the signal sequence and FLAG-epitope tag encoded by the vector. The cDNA encoding the extracellular domain of TR10 (amino acids 56–210) was obtained by PCR, similar to the methods described above, and subcloned into a modified pCMV1FLAG vector that allowed for in-frame fusion with the Fc portion of human IgG. DR4-Fc, TNRF1-Fc, Fc and soluble TRAIL and TNF alpha expression constructs have been described previously, Pan, G. et al., Science 276:111–113 (1997), which is incorporated herein by reference in its entirety.

The receptor-Fc fusions and soluble ligands were prepared and in vivo binding was performed as previously described, Pan G. et al., Science 276:111–113 (1997), and Pan G. et al., Science 277:815–818 (1997), both of which are incorporated herein by reference in their entirety.

Cell death blocking assays using receptor-Fc fusions were carried out as described previously by Pan G. et al., Science 276:111–113 (1997), and Pan G. et al., Science 277:815–818 (1997), both of which are incorporated herein by reference in their entirety.

Results

The extracellular domain of TR10 was expressed as a secreted chimera fused to the Fc portion of human IgG in 293 cells. Conditioned medium from transfected cells was mixed with bacterially expressed soluble His-FLAG-tagged TRAIL. The resulting complex was precipitated with protein G-Sepharose and bound TRAIL detected by Western blotting with anti-FLAG antibody. Like DR4, DR5, and TR5

(TRID), TR10 bound TRAIL. Corroborating this ability to bind TRAIL was the finding that TR10-Fc, like DR4-Fc, could efficiently block TRAIL-induced apoptosis.

In keeping with TR10 possessing a truncated non-functional death domain was the observation that TR10 overexpression did not cause cell death in Hela cells, and as might be expected, could act as a dominant negative receptor antagonizing TRAIL-induced apoptosis. Therefore, ectopic expression of TR10, like that of the decoy receptor TR5, is capable of substantially attenuating TRAIL-induced cell death, suggesting that TR10 antagonizes TRAIL signaling.

It will be clear that the invention may be practiced otherwise than as particularly described in the foregoing description and examples.

Numerous modifications and variations of the present invention are possible in light of the above teachings and, therefore, are within the scope of the appended claims.

The entire disclosure of all publications (including patents, patent applications, journal articles, laboratory manuals, books, or other documents) cited herein are hereby incorporated by reference.

What is claimed is:

1. An isolated nucleic acid molecule comprising a polynucleotide sequence selected from the group consisting of:
   (a) a polynucleotide sequence encoding amino acid residues −55 to 331 of SEQ ID NO:2;
   (b) a polynucleotide sequence encoding amino acid residues −54 to 331 of SEQ ID NO:2;
   (c) a polynucleotide sequence encoding amino acid residues 1 to 157 of SEQ ID NO:2;
   (d) a polynucleotide sequence encoding amino acid residues 158 to 175 of SEQ ID NO:2;
   (e) a polynucleotide sequence encoding amino acid residues 176 to 331 of SEQ ID NO:2;
   (f) a polynucleotide sequence encoding amino acid residues 298 to 308 of SEQ ID NO:2; and
   (g) a polynucleotide sequence encoding a fragment of the polypeptide of SEQ ID NO:2 wherein said fragment binds a Tumor Necrosis Factor (TNF)-family ligand.

2. The isolated nucleic acid molecule of claim 1 which comprises polynucleotide sequence (a).

3. The isolated nucleic acid molecule of claim 1 which comprises polynucleotide sequence (b).

4. The isolated nucleic acid molecule of claim 1 which comprises polynucleotide sequence (c).

5. The isolated nucleic acid molecule of claim 1 which comprises polynucleotide sequence (d).

6. The isolated nucleic acid molecule of claim 1 which comprises polynucleotide sequence (e).

7. The isolated nucleic acid molecule of claim 1 which comprises polynucleotide sequence (f).

8. The isolated nucleic acid molecule of claim 1 which comprises polynucleotide sequence (g).

9. The isolated nucleic acid molecule of claim 8 wherein said Tumor Necrosis Factor (TNF)-family ligand is TRAIL.

10. The isolated nucleic acid molecule of claim 1 wherein the polynucleotide sequence further comprises a heterologous polynucleotide sequence.

11. The isolated nucleic acid molecule of claim 10 wherein the heterologous polynucleotide sequence encodes a heterologous polypeptide.

12. The isolated nucleic acid molecule of claim 11 wherein the heterologous polypeptide is the Fc domain of immunoglobulin.

13. A recombinant vector comprising the isolated nucleic acid molecule of claim 1.

14. The recombinant vector of claim 13 wherein the nucleic acid molecule is operably associated with a heterologous regulatory sequence that controls gene expression.

15. A recombinant host cell comprising the isolated nucleic acid molecule of claim 1.

16. The recombinant host cell of claim 15 wherein the nucleic acid molecule is operably associated with a heterologous regulatory sequence that controls gene expression.

17. A method for producing a polypeptide encoded by the nucleic acid molecule of claim 1, comprising:
   (a) culturing a host cell comprising the nucleic acid molecule under conditions suitable to produce the polypeptide; and
   (b) recovering the polypeptide from the cell culture.

18. An isolated nucleic acid molecule comprising a polynucleotide sequence selected from the group consisting of:
   (a) a polynucleotide sequence encoding the full-length polypeptide having the amino acid sequence encoded by the cDNA plasmid contained in ATCC Deposit No. 209040;
   (b) a polynucleotide sequence encoding the full-length polypeptide excluding the N-terminal methionine residue, having the amino acid sequence encoded by the cDNA plasmid contained in ATCC Deposit No. 209040;
   (c) a polynucleotide sequence encoding the extracellular domain of the polypeptide having the amino acid sequence encoded by the cDNA plasmid contained in ATCC Deposit No. 209040;
   (d) a polynucleotide sequence encoding the partial death domain of the polypeptide having the amino acid sequence encoded by the cDNA plasmid contained in ATCC Deposit No. 209040; and
   (e) a polynucleotide sequence encoding a fragment of the polypeptide having the amino acid sequence encoded by the cDNA plasmid contained in ATCC Deposit No. 209040 wherein said fragment binds a Tumor Necrosis Factor (TNF)-family ligand.

19. The isolated nucleic acid molecule of claim 18 which comprises polynucleotide sequence (a).

20. The isolated nucleic acid molecule of claim 18 which comprises polynucleotide sequence (b).

21. The isolated nucleic acid molecule of claim 18 which comprises polynucleotide sequence (c).

22. The isolated nucleic acid molecule of claim 18 which comprises polynucleotide sequence (d).

23. The isolated nucleic acid molecule of claim 18 which comprises polynucleotide sequence (e).

24. The isolated nucleic acid molecule of claim 23 wherein said Tumor Necrosis Factor (TNF)-family ligand is TRAIL.

25. The isolated nucleic acid molecule of claim 18 wherein the polynucleotide sequence further comprises a heterologous polynucleotide sequence.

26. The isolated nucleic acid molecule of claim 25 wherein the heterologous polynucleotide sequence encodes a heterologous polypeptide.

27. The isolated nucleic acid molecule of claim 26 wherein the heterologous polypeptide is the Fc domain of immunoglobulin.

28. A recombinant vector comprising the isolated nucleic acid molecule of claim 18.

29. The recombinant vector of claim 28 wherein the nucleic acid molecule is operably associated with a heterologous regulatory sequence that controls gene expression.

30. A recombinant host cell comprising the isolated nucleic acid molecule of claim 18.

31. The recombinant host cell of claim 30 wherein the nucleic acid molecule is operably associated with a heterologous regulatory sequence that controls gene expression.

32. A method for producing a polypeptide encoded by the nucleic acid molecule of claim 18, comprising:
   (a) culturing a host cell comprising the nucleic acid molecule under conditions suitable to produce the polypeptide; and
   (b) recovering the polypeptide from the cell culture.

33. An isolated nucleic acid molecule comprising a polynucleotide sequence selected from the group consisting of:
   (a) a polynucleotide sequence of at least 50 contiguous nucleotides of nucleotides 109 to 1269 of SEQ ID NO:1; and
   (b) a polynucleotide complementary to polynucleotide sequence (a).

34. The isolated nucleic acid of claim 33 which comprises polynucleotide sequence (a).

35. The isolated nucleic acid molecule of claim 34 which encodes a polypeptide which binds a Tumor Necrosis Factor (TNF)-family ligand.

36. The isolated nucleic acid molecule of claim 35 which encodes a polypeptide which binds TRAIL.

37. The isolated nucleic acid of claim 33 which comprises polynucleotide sequence (b).

38. The isolated nucleic acid molecule of claim 33 wherein the polynucleotide sequence further comprises a heterologous polynucleotide sequence.

39. The isolated nucleic acid molecule of claim 38 wherein the heterologous polynucleotide sequence encodes a heterologous polypeptide.

40. The isolated nucleic acid molecule of claim 39 wherein the heterologous polypeptide is the Fc domain of immunoglobulin.

41. A recombinant vector comprising the isolated nucleic acid molecule of claim 33.

42. The recombinant vector of claim 41 wherein the nucleic acid molecule is operably associated with a heterologous regulatory sequence that controls gene expression.

43. A recombinant host cell comprising the isolated nucleic acid molecule of claim 33.

44. The recombinant host cell of claim 43 wherein the nucleic acid molecule is operably associated with a heterologous regulatory sequence that controls gene expression.

45. A method for producing a polypeptide encoded by the nucleic acid molecule of claim 33, comprising:
    (a) culturing a host cell comprising the nucleic acid molecule under conditions suitable to produce the polypeptide; and
    (b) recovering the polypeptide from the cell culture.

46. An isolated nucleic acid molecule comprising a polynucleotide sequence selected from the group comprising:
    (a) a polynucleotide sequence of at least 50 contiguous nucleotides of the open reading frame encoded by the cDNA plasmid contained in ATCC Deposit No. 209040; and
    (b) a polynucleotide complementary to polynucleotide sequence (a).

47. The isolated nucleic acid molecule of claim 46 which comprises polynucleotide sequence (a).

48. The isolated nucleic acid molecule of claim 47 which encodes a polypeptide which binds a Tumor Necrosis Factor (TNF)-family ligand.

49. The isolated nucleic acid molecule of claim 48 wherein said Tumor Necrosis Factor (TNF)-family ligand is TRAIL.

50. The isolated nucleic acid molecule of claim 46 which comprises polynucleotide sequence (b).

51. The isolated nucleic acid molecule of claim 46 wherein the polynucleotide sequence further comprises a heterologous polynucleotide sequence.

52. The isolated nucleic acid molecule of claim 51 wherein the heterologous polynucleotide sequence encodes a heterologous polypeptide.

53. The isolated nucleic acid molecule of claim 52 wherein the heterologous polypeptide is the Fc domain of immunoglobulin.

54. A recombinant vector comprising the isolated nucleic acid molecule of claim 46.

55. The recombinant vector of claim 54 wherein the nucleic acid molecule is operably associated with a heterologous regulatory sequence that controls gene expression.

56. A recombinant host cell comprising the isolated nucleic acid molecule of claim 46.

57. The recombinant host cell of claim 56 wherein the nucleic acid molecule is operably associated with a heterologous regulatory sequence that controls gene expression.

58. A method for producing a polypeptide encoded by the nucleic acid molecule of claim 46, comprising:
    (a) culturing a host cell comprising the nucleic acid molecule under conditions suitable to produce the polypeptide; and
    (b) recovering the polypeptide from the cell culture.

59. An isolated nucleic acid molecule comprising a polynucleotide sequence encoding at least 30 contiguous amino acid residues of positions −55 to +331 of SEQ ID NO:2.

60. The isolated nucleic acid molecule of claim 59 which comprises a polynucleotide sequence encoding at least 50 contiguous amino acid residues of positions −55 to +331 of SEQ ID NO:2.

61. The isolated nucleic acid molecule of claim 59 which encodes a polypeptide which binds a Tumor Necrosis Factor (TNF)-family ligand.

62. The isolated nucleic acid molecule of claim 61 which encodes a polypeptide which binds TRAIL.

63. The isolated nucleic acid molecule of claim 59 wherein the polynucleotide sequence further comprises a heterologous polynucleotide sequence.

64. The isolated nucleic acid molecule of claim 63 wherein the heterologous polynucleotide sequence encodes a heterologous polypeptide.

65. The isolated nucleic acid molecule of claim 64 wherein the heterologous polypeptide is the Fc domain of immunoglobulin.

66. A recombinant vector comprising the isolated nucleic acid molecule of claim 59.

67. The recombinant vector of claim 66 wherein the nucleic acid molecule is operably associated with a heterologous regulatory sequence that controls gene expression.

68. A recombinant host cell comprising the isolated nucleic acid molecule of claim 59.

69. The recombinant host cell of claim 68 wherein the nucleic acid molecule is operably associated with a heterologous regulatory sequence that controls gene expression.

70. A method for producing a polypeptide encoded by the nucleic acid molecule of claim 59, comprising:
    (a) culturing a host cell comprising the nucleic acid molecule under conditions suitable to produce the polypeptide; and
    (b) recovering the polypeptide from the cell culture.

71. An isolated nucleic acid molecule comprising a polynucleotide sequence encoding at least 30 contiguous amino acid residues of the open reading frame encoded by the cDNA plasmid contained in ATCC Deposit No. 209040.

72. The isolated polynucleotide of claim 71 which comprises a polynucleotide sequence encoding at least 50 contiguous amino acid residues of the open reading frame encoded by the cDNA plasmid contained in ATCC Deposit No. 209040.

73. The isolated nucleic acid molecule of claim 71 which encodes a polypeptide which binds a Tumor Necrosis Factor (TNF)-family ligand.

74. The isolated nucleic acid molecule of claim 73 which encodes a polypeptide which binds TRAIL.

75. The isolated nucleic acid molecule of claim 71 wherein the polynucleotide sequence further comprises a heterologous polynucleotide sequence.

76. The isolated nucleic acid molecule of claim 75 wherein the heterologous polynucleotide sequence encodes a heterologous polypeptide.

77. The isolated nucleic acid molecule of claim 76 wherein the heterologous polypeptide is the Fc domain of immunoglobulin.

78. A recombinant vector comprising the isolated nucleic acid molecule of claim 71.

79. The recombinant vector of claim 78 wherein the nucleic acid molecule is operably associated with a heterologous regulatory sequence that controls gene expression.

80. A recombinant host cell comprising the isolated nucleic acid molecule of claim 71.

81. The recombinant host cell of claim 80 wherein the nucleic acid molecule is operably associated with a heterologous regulatory sequence that controls gene expression.

82. A method for producing a polypeptide encoded by the nucleic acid molecule of claim 71, comprising:
 (a) culturing a host cell comprising the nucleic acid molecule under conditions suitable to produce the polypeptide; and
 (b) recovering the polypeptide from the cell culture.

83. An isolated nucleic acid molecule comprising a first polynucleotide sequence 95% or more identical to a second polynucleotide sequence selected from the group consisting of:
 (a) a polynucleotide sequence encoding amino acid residues −55 to 331 of SEQ ID NO:2;
 (b) a polynucleotide sequence encoding amino acid residues −54 to 331 of SEQ ID NO:2;
 (c) a polynucleotide sequence encoding amino acid residues 1 to 331 of SEQ ID NO:2;
 (d) a polynucleotide sequence encoding amino acid residues 1 to 157 of SEQ ID NO:2;
 (e) a polynucleotide sequence encoding amino acid residues 158 to 175 of SEQ ID NO:2; and
 (f) a polynucleotide sequence encoding amino acid residues 176 to 331 of SEQ ID NO:2.

84. The isolated nucleic acid molecule of claim 83 wherein said second polynucleotide sequence is (a).

85. The isolated nucleic acid molecule of claim 83 wherein said second polynucleotide sequence is (b).

86. The isolated nucleic acid molecule of claim 83 wherein said second polynucleotide sequence is (c).

87. The isolated nucleic acid molecule of claim 83 wherein said second polynucleotide sequence is (d).

88. The isolated nucleic acid molecule of claim 83 wherein said second polynucleotide sequence is (e).

89. The isolated nucleic acid molecule of claim 83 wherein said second polynucleotide sequence is (f).

90. The isolated nucleic acid molecule of claim 83 which encodes a polypeptide which binds a Tumor Necrosis Factor (TNF)-family ligand.

91. The isolated nucleic acid molecule of claim 90 which encodes a polypeptide which binds TRAIL.

92. The isolated nucleic acid of claim 83 wherein the polynucleotide sequence further comprises a heterologous polynucleotide sequence.

93. The isolated nucleic acid of claim 92 wherein the heterologous polynucleotide sequence encodes a heterologous polypeptide.

94. The isolated nucleic acid molecule of claim 93 wherein the heterologous polypeptide is the Fc domain of immunoglobulin.

95. A recombinant vector comprising the isolated nucleic acid molecule of claim 83.

96. The recombinant vector of claim 95 wherein the nucleic acid molecule is operably associated with a heterologous regulatory sequence that controls gene expression.

97. A recombinant host cell comprising the isolated nucleic acid molecule of claim 83.

98. The recombinant host cell of claim 97 wherein the nucleic acid molecule is operably associated with a heterologous regulatory sequence that controls gene expression.

99. A method for producing a polypeptide encoded by the nucleic acid molecule of claim 83, comprising:
 (a) culturing a host cell comprising the nucleic acid molecule under conditions suitable to produce the polypeptide; and
 (b) recovering the polypeptide from the cell culture.

100. An isolated nucleic acid molecule comprising a polynucleotide which hybridizes to the complement of nucleotides 109 to 1269 of the polynucleotide shown as SEQ ID NO:1, wherein said hybridization occurs under conditions comprising hybridization in a solution consisting of 50% formamide, 5×SSC, 50 mM sodium phosphate (pH 7.6), 5×Denhardt's solution, 10% dextran sulfate, and 20 μg/ml denatured, sheared salmon sperm DNA overnight at 42° C. and wash in a solution consisting of 0.1×SSC at 65° C. wherein said isolated nucleic acid molecule encodes a polypeptide which binds a Tumor Necrosis Factor (TNF)-family ligand.

101. The isolated nucleic acid molecule of claim 100 which encodes a polypeptide which binds TRAIL.

102. The isolated nucleic acid molecule of claim 100 wherein the polynucleotide sequence further comprises a heterologous polynucleotide sequence.

103. The isolated nucleic acid molecule of claim 102 wherein the heterologous polynucleotide sequence encodes a heterologous polypeptide.

104. The isolated nucleic acid molecule of claim 103 wherein the heterologous polypeptide is the Fc domain of immunoglobulin.

105. A recombinant vector comprising the isolated nucleic acid molecule of claim 100.

106. The recombinant vector of claim 105 wherein the nucleic acid molecule is operably associated with a heterologous regulatory sequence that controls gene expression.

107. A recombinant host cell comprising the isolated nucleic acid molecule of claim 100.

108. The recombinant host cell of claim 107 wherein the nucleic acid molecule is operably associated with a heterologous regulatory sequence that controls gene expression.

109. A method for producing a polypeptide encoded by the nucleic acid molecule of claim 100, comprising:
 (a) culturing a host cell comprising the nucleic acid molecule under conditions suitable to produce the polypeptide; and
 (b) recovering the polypeptide from the cell culture.

* * * * *

SEQUENCE LISTING (1) GENERAL INFORMATION:

(iii) NUMBER OF SEQUENCES: 15

(2) INFORMATION FOR SEQ ID NO:1:

(i) SEQUENCE CHARACTERISTICS:
        (A) LENGTH: 3566 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 109..1266

(ix) FEATURE:
        (A) NAME/KEY: sig_peptide
        (B) LOCATION: 109..271

(ix) FEATURE:
        (A) NAME/KEY: mat_peptide
        (B) LOCATION: 274..1266

(xi) SEQUENCE DESCRIPTION: SEQ ID NO:1:

```
CGACCCACGC GTCCGCCCAC GCGTCCGGAG AACCTTTGCA CGCGCACAAA CTACGGGGAC        60

GATTTCTGAT TGATTTTTGG CGCTTTCGAT CCACCCTCCT CCCTTCTC ATG GGA CTT       117
                                                    Met Gly Leu
                                                    -55

TGG GGA CAA AGC GTC CCG ACC GCC TCG AGC GCT CGA GCA GGG CGC TAT        165
Trp Gly Gln Ser Val Pro Thr Ala Ser Ser Ala Arg Ala Gly Arg Tyr
        -50             -45                 -40

CCA GGA GCC AGG ACA GCG TCG GGA ACC AGA CCA TGG CTC CTG GAC CCC        213
Pro Gly Ala Arg Thr Ala Ser Gly Thr Arg Pro Trp Leu Leu Asp Pro
    -35                 -30                 -25

AAG ATC CTT AAG TTC GTC GTC TTC ATC GTC GCG GTT CTG CTG CCG GTC        261
Lys Ile Leu Lys Phe Val Val Phe Ile Val Ala Val Leu Leu Pro Val
-20                 -15                 -10                  -5

CGG GTT GAC TCT GCC ACC ATC CCC CGG CAG GAC GAA GTT CCC CAG CAG        309
Arg Val Asp Ser Ala Thr Ile Pro Arg Gln Asp Glu Val Pro Gln Gln
                    1               5                   10

ACA GTG GCC CCA CAG CAA CAG AGG CGC AGC CTC AAG GAG GAG GAG TGT        357
Thr Val Ala Pro Gln Gln Gln Arg Arg Ser Leu Lys Glu Glu Glu Cys
                15                  20                  25

CCA GCA GGA TCT CAT AGA TCA GAA TAT ACT GGA GCC TGT AAC CCG TGC        405
Pro Ala Gly Ser His Arg Ser Glu Tyr Thr Gly Ala Cys Asn Pro Cys
        30                  35                  40
```

```
ACA GAG GGT GTG GAT TAC ACC ATT GCT TCC AAC AAT TTG CCT TCT TGC     453
Thr Glu Gly Val Asp Tyr Thr Ile Ala Ser Asn Asn Leu Pro Ser Cys
 45                  50                  55                  60

CTG CTA TGT ACA GTT TGT AAA TCA GGT CAA ACA AAT AAA AGT TCC TGT     501
Leu Leu Cys Thr Val Cys Lys Ser Gly Gln Thr Asn Lys Ser Ser Cys
                 65                  70                  75

ACC ACG ACC AGA GAC ACC GTG TGT CAG TGT GAA AAA GGA AGC TTC CAG     549
Thr Thr Thr Arg Asp Thr Val Cys Gln Cys Glu Lys Gly Ser Phe Gln
             80                  85                  90

GAT AAA AAC TCC CCT GAG ATG TGC CGG ACG TGT AGA ACA GGG TGT CCC     597
Asp Lys Asn Ser Pro Glu Met Cys Arg Thr Cys Arg Thr Gly Cys Pro
         95                 100                 105

AGA GGG ATG GTC AAG GTC AGT AAT TGT ACG CCC CGG AGT GAC ATC AAG     645
Arg Gly Met Val Lys Val Ser Asn Cys Thr Pro Arg Ser Asp Ile Lys
    110                 115                 120

TGC AAA AAT GAA TCA GCT GCC AGT TCC ACT GGG AAA ACC CCA GCA GCG     693
Cys Lys Asn Glu Ser Ala Ala Ser Ser Thr Gly Lys Thr Pro Ala Ala
125                 130                 135                 140

GAG GAG ACA GTG ACC ACC ATC CTG GGG ATG CTT GCC TCT CCC TAT CAC     741
Glu Glu Thr Val Thr Thr Ile Leu Gly Met Leu Ala Ser Pro Tyr His
                145                 150                 155

TAC CTT ATC ATC ATA GTG GTT TTA GTC ATC ATT TTA GCT GTG GTT GTG     789
Tyr Leu Ile Ile Ile Val Val Leu Val Ile Ile Leu Ala Val Val Val
            160                 165                 170

GTT GGC TTT TCA TGT CGG AAG AAA TTC ATT TCT TAC CTC AAA GGC ATC     837
Val Gly Phe Ser Cys Arg Lys Lys Phe Ile Ser Tyr Leu Lys Gly Ile
        175                 180                 185

TGC TCA GGT GGT GGA GGA GGT CCC GAA CGT GTG CAC AGA GTC CTT TTC     885
Cys Ser Gly Gly Gly Gly Gly Pro Glu Arg Val His Arg Val Leu Phe
    190                 195                 200

CGG CGG CGT TCA TGT CCT TCA CGA GTT CCT GGG GCG GAG GAC AAT GCC     933
Arg Arg Arg Ser Cys Pro Ser Arg Val Pro Gly Ala Glu Asp Asn Ala
205                 210                 215                 220

CGC AAC GAG ACC CTG AGT AAC AGA TAC TTG CAG CCC ACC CAG GTC TCT     981
Arg Asn Glu Thr Leu Ser Asn Arg Tyr Leu Gln Pro Thr Gln Val Ser
                225                 230                 235

GAG CAG GAA ATC CAA GGT CAG GAG CTG GCA GAG CTA ACA GGT GTG ACT    1029
Glu Gln Glu Ile Gln Gly Gln Glu Leu Ala Glu Leu Thr Gly Val Thr
            240                 245                 250

GTA GAG TCG CCA GAG GAG CCA CAG CGT CTG CTG GAA CAG GCA GAA GCT    1077
Val Glu Ser Pro Glu Glu Pro Gln Arg Leu Leu Glu Gln Ala Glu Ala
        255                 260                 265

GAA GGG TGT CAG AGG AGG AGG CTG CTG GTT CCA GTG AAT GAC GCT GAC    1125
Glu Gly Cys Gln Arg Arg Arg Leu Leu Val Pro Val Asn Asp Ala Asp
    270                 275                 280

TCC GCT GAC ATC AGC ACC TTG CTG GAT GCC TCG GCA ACA CTG GAA GAA    1173
Ser Ala Asp Ile Ser Thr Leu Leu Asp Ala Ser Ala Thr Leu Glu Glu
285                 290                 295                 300

GGA CAT GCA AAG GAA ACA ATT CAG GAC CAA CTG GTG GGC TCC GAA AAG    1221
Gly His Ala Lys Glu Thr Ile Gln Asp Gln Leu Val Gly Ser Glu Lys
                305                 310                 315

CTC TTT TAT GAA GAA GAT GAG GCA GGC TCT GCT ACG TCC TGC CTG        1266
Leu Phe Tyr Glu Glu Asp Glu Ala Gly Ser Ala Thr Ser Cys Leu
            320                 325                 330

TGAAAGAATC TCTTCAGGAA ACCAGAGCTT CCCTCATTTA CCTTTTCTCC TACAAAGGGA  1326

AGCAGCCTGG AAGAAACAGT CCAGTACTTG ACCCATGCCC CAACAAACTC TACTATCCAA  1386

TATGGGGCAG CTTACCAATG GTCCTAGAAC TTTGTTAACG CACTTGGAGT AATTTTTATG  1446

AAATACTGCG TGTGATAAGC AAACGGGAGA AATTTATATC AGATTCTTGG CTGCATAGTT  1506
```

```
ATACGATTGT GTATTAAGGG TCGTTTTAGG CCACATGCGG TGGCTCATGC CTGTAATCCC    1566

AGCACTTTGA TAGGCTGAGG CAGGTGGATT GCTTTGAGCT CGGGAGTTTG AGACCAGCCT    1626

CATCAACACA GTGAAACTCC ATCTCAATTT AAAAAGAAAA AAAAGTGGTT TTAGGATGTC    1686

ATTCTTTGCA GTTCTTCATC ATGAGACAAG TCTTTTTTTC TGCTTCTTAT ATTGCAAGCT    1746

CCATCTCTAC TGGTGTGTGC ATTTAATGAC ATCTAACTAC AGATGCCGCA CAGCCACAAT    1806

GCTTTGCCTT ATAGTTTTTT AACTTTAGAA CGGGATTATC TTGTTATTAC CTGTATTTTC    1866

AGTTTCGGAT ATTTTTGACT TAATGATGAG ATTATCAAGA CGTAGCCCTA TGCTAAGTCA    1926

TGAGCATATG GACTTACGAG GGTTCGACTT AGAGTTTTGA GCTTTAAGAT AGGATTATTG    1986

GGGCTTACCC CCACCTTAAT TAGAGAAACA TTTATATTGC TTACTACTGT AGGCTGTACA    2046

TCTCTTTTCC GATTTTTGTA TAATGATGTA ACATGGAAA AACTTTAGGA AATGCACTTA    2106

TTAGGCTGTT TACATGGGTT GCCTGGATAC AAATCAGCAG TCAAAAATGA CTAAAAATAT    2166

AACTAGTGAC GGAGGGAGAA ATCCTCCCTC TGTGGGAGGC ACTTACTGCA TTCCAGTTCT    2226

CCCTCCTGCG CCCTGAGACT GGACCAGGGT TTGATGGCTG GCAGCTTCTC AAGGGGCAGC    2286

TTGTCTTACT TGTTAATTTT AGAGGTATAT AGCCATATTT ATTTATAAAT AAATATTTAT    2346

TTATTTATTT ATAAGTAGAT GTTTACATAT GCCCAGGATT TTGAAGAGCC TGGTATCTTT    2406

GGGAAGCCAT GTGTCTGGTT TGTCGTGCTG GGACAGTCAT GGGACTGCAT CTTCCGACTT    2466

GTCCACAGCA GATGAGGACA GTGAGAATTA AGTTAGATCC GAGACTGCGA AGAGCTTCTC    2526

TTTCAAGCGC CATTACAGTT GAACGTTAGT GAATCTTGAG CCTCATTTGG GCTCAGGGCA    2586

GAGCAGGTGT TTATCTGCCC CGGCATCTGC CATGGCATCA AGAGGGAAGA GTGGACGGTG    2646

CTTGGGAATG GTGTGAAATG GTTGCCGACT CAGGCATGGA TGGGCCCCTC TCGCTTCTGG    2706

TGGTCTGTGA ACTGAGTCCC TGGGATGCCT TTTAGGGCAG AGATTCCTGA GCTGCGTTTT    2766

AGGGTACAGA TTCCCTGTTT GAGGAGCTTG GCCCCTCTGT AAGCATCTGA CTCATCTCAG    2826

AGATATCAAT TCTTAAACAC TGTGACAACG GGATCTAAAA TGGCTGACAC ATTTGTCCTT    2886

GTGTCACGTT CCATTATTTT ATTTAAAAAC CTCAGTAATC GTTTTAGCTT CTTTCCAGCA    2946

AACTCTTCTC CACAGTAGCC CAGTCGTGGT AGGATAAATT ACGGATATAG TCATTCTAGG    3006

GGTTTCAGTC TTTTCCATCT CAAGGCATTG TGTGTTTTGT TCCGGGACTG GTTTGGCTGG    3066

GACAAAGTTA GAACTGCCTG AAGTTCGCAC ATTCAGATTG TTGTGTCCAT GGAGTTTTAG    3126

GAGGGGATGG CCTTTCCGGT CTTCGCACTT CCATCCTCTC CCCACTTCCC ATCTGGCGTC    3186

CCACACCTTG TCCCCCTGCA CTTCTGGATG ACCAGGGTGC TGCTGCCTCC TAGTCTTTGC    3246

CTTTGCTGGG CCTTCTGTGC AGGAGACTTG GTCTCAAAGC TCAGAGAGAG CCAGTCCGGT    3306

CCCAGCTCCT TTGTCCCTTC CTCAGAGGCC TTCCTTGAAG ATGCATCTAG ACTACCAGCC    3366

TTATCAGTGT TTAAGCTTAT TCCTTTAACA TAAGCTTCCT GACAACATGA AATTGTTGGG    3426

GTTTTTTGGC GTTTGTTGAT TTGTTTAGGT TTTGCTTTAT ACCCGGGCCA AATAGCACAT    3486

AACACCTGGT TATATATGAA ATACTCATAT GTTTATGACC AAAATAAATA TGAAACCTCA    3546

AAAAAAAAAA AAAAAAAAA                                                 3566
```

(2) INFORMATION FOR SEQ ID NO:2:

(i) SEQUENCE CHARACTERISTICS:
        (A) LENGTH: 386 amino acids
        (B) TYPE: amino acid
        (D) TOPOLOGY: linear (ii) MOLECULE TYPE: protein (xi) SEQUENCE DESCRIPTION: SEQ ID NO:2:

```
Met Gly Leu Trp Gly Gln Ser Val Pro Thr Ala Ser Ser Arg Ala
-55             -50                 -45                 -40

Gly Arg Tyr Pro Gly Ala Arg Thr Ala Ser Gly Thr Arg Pro Trp Leu
            -35                 -30                 -25

Leu Asp Pro Lys Ile Leu Lys Phe Val Val Phe Ile Val Ala Val Leu
            -20                 -15                 -10

Leu Pro Val Arg Val Asp Ser Ala Thr Ile Pro Arg Gln Asp Glu Val
        -5                   1               5

Pro Gln Gln Thr Val Ala Pro Gln Gln Arg Arg Ser Leu Lys Glu
 10              15                  20                  25

Glu Glu Cys Pro Ala Gly Ser His Arg Ser Glu Tyr Thr Gly Ala Cys
                30                  35                  40

Asn Pro Cys Thr Glu Gly Val Asp Tyr Thr Ile Ala Ser Asn Asn Leu
                45                  50                  55

Pro Ser Cys Leu Leu Cys Thr Val Cys Lys Ser Gly Gln Thr Asn Lys
                60                  65                  70

Ser Ser Cys Thr Thr Thr Arg Asp Thr Val Cys Gln Cys Glu Lys Gly
 75                  80                  85

Ser Phe Gln Asp Lys Asn Ser Pro Glu Met Cys Arg Thr Cys Arg Thr
 90                  95                 100                 105

Gly Cys Pro Arg Gly Met Val Lys Val Ser Asn Cys Thr Pro Arg Ser
                110                 115                 120

Asp Ile Lys Cys Lys Asn Glu Ser Ala Ala Ser Ser Thr Gly Lys Thr
                125                 130                 135

Pro Ala Ala Glu Glu Thr Val Thr Thr Ile Leu Gly Met Leu Ala Ser
                140                 145                 150

Pro Tyr His Tyr Leu Ile Ile Ile Val Val Leu Val Ile Ile Leu Ala
                155                 160                 165

Val Val Val Val Gly Phe Ser Cys Arg Lys Lys Phe Ile Ser Tyr Leu
170                 175                 180                 185

Lys Gly Ile Cys Ser Gly Gly Gly Gly Pro Glu Arg Val His Arg
                190                 195                 200

Val Leu Phe Arg Arg Arg Ser Cys Pro Ser Arg Val Pro Gly Ala Glu
                205                 210                 215

Asp Asn Ala Arg Asn Glu Thr Leu Ser Asn Arg Tyr Leu Gln Pro Thr
                220                 225                 230

Gln Val Ser Glu Gln Glu Ile Gln Gly Gln Glu Leu Ala Glu Leu Thr
 235                 240                 245

Gly Val Thr Val Glu Ser Pro Glu Glu Pro Gln Arg Leu Leu Glu Gln
250                 255                 260                 265

Ala Glu Ala Glu Gly Cys Gln Arg Arg Arg Leu Leu Val Pro Val Asn
                270                 275                 280

Asp Ala Asp Ser Ala Asp Ile Ser Thr Leu Leu Asp Ala Ser Ala Thr
                285                 290                 295

Leu Glu Glu Gly His Ala Lys Glu Thr Ile Gln Asp Gln Leu Val Gly
                300                 305                 310

Ser Glu Lys Leu Phe Tyr Glu Glu Asp Glu Ala Gly Ser Ala Thr Ser
 315                 320                 325

Cys Leu
330
```

(2) INFORMATION FOR SEQ ID NO:3:

(i) SEQUENCE CHARACTERISTICS:
        (A) LENGTH: 331 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:3:

```
Met Leu Gly Ile Trp Thr Leu Leu Pro Leu Val Leu Thr Ser Val Ala
  1               5                  10                  15

Arg Leu Ser Ser Lys Ser Val Asn Ala Gln Val Thr Asp Ile Asn Ser
             20                  25                  30

Lys Gly Leu Glu Leu Arg Lys Thr Val Thr Val Glu Thr Gln Asn Leu
         35                  40                  45

Glu Gly Leu His His Asp Gly Gln Phe Cys His Pro Cys Pro Pro Gly
     50                  55                  60

Glu Arg Lys Ala Arg Asp Cys Thr Val Asn Gly Asp Glu Pro Asp Cys
 65                  70                  75                  80

Val Pro Cys Gln Glu Gly Lys Glu Tyr Thr Asp Lys Ala His Phe Ser
                 85                  90                  95

Ser Lys Cys Arg Arg Cys Arg Leu Cys Asp Glu Gly His Gly Leu Glu
            100                 105                 110

Val Glu Ile Asn Cys Thr Arg Thr Gln Asn Thr Lys Cys Arg Cys Lys
        115                 120                 125

Pro Asn Phe Phe Cys Asn Ser Thr Val Cys Glu His Cys Asp Pro Cys
    130                 135                 140

Thr Lys Cys Glu His Gly Ile Ile Lys Glu Cys Thr Leu Thr Ser Asn
145                 150                 155                 160

Thr Lys Cys Lys Glu Glu Gly Ser Arg Ser Asn Gly Trp Leu Cys Leu
                165                 170                 175

Leu Leu Leu Pro Ile Pro Leu Ile Val Trp Val Lys Arg Lys Glu Val
            180                 185                 190

Gln Lys Thr Cys Arg Lys His Arg Lys Glu Asn Gln Gly Ser His Glu
        195                 200                 205

Ser Pro Thr Leu Asn Pro Glu Thr Val Ala Ile Asn Leu Ser Asp Val
    210                 215                 220

Asp Leu Ser Lys Tyr Ile Thr Thr Ile Ala Gly Val Met Thr Leu Ser
225                 230                 235                 240

Gln Val Lys Gly Phe Val Arg Lys Asn Gly Val Asn Glu Ala Lys Ile
                245                 250                 255

Asp Glu Ile Lys Asn Asp Asn Val Gln Asp Thr Ala Glu Gln Lys Val
            260                 265                 270

Gln Leu Leu Arg Asn Trp His Gln Leu His Gly Lys Lys Glu Ala Tyr
        275                 280                 285

Asp Thr Leu Ile Lys Asp Leu Lys Lys Ala Asn Leu Cys Thr Leu Ala
    290                 295                 300

Glu Lys Ile Thr Ile Ile Leu Lys Asp Ile Thr Ser Asp Ser Glu Asn
305                 310                 315                 320

Ser Asn Phe Arg Asn Glu Ile Gln Ser Leu Val
                325                 330
```

(2) INFORMATION FOR SEQ ID NO:4:

(i) SEQUENCE CHARACTERISTICS:
        (A) LENGTH: 427 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:4:

```
Met Gly Ala Gly Ala Thr Gly Arg Ala Met Asp Gly Pro Arg Leu Leu
 1               5                  10                  15

Leu Leu Leu Leu Leu Gly Val Ser Leu Gly Gly Ala Lys Glu Ala Cys
                20                  25                  30

Pro Thr Gly Leu Tyr Thr His Ser Gly Glu Cys Cys Lys Ala Cys Asn
                35                  40                  45

Leu Gly Glu Gly Val Ala Gln Pro Cys Gly Ala Asn Gln Thr Val Cys
    50                  55                  60

Glu Pro Cys Leu Asp Ser Val Thr Phe Ser Asp Val Val Ser Ala Thr
65                  70                  75                  80

Glu Pro Cys Lys Pro Cys Thr Glu Cys Val Gly Leu Gln Ser Met Ser
                85                  90                  95

Ala Pro Cys Val Glu Ala Asp Asp Ala Val Cys Arg Cys Ala Tyr Gly
                100                 105                 110

Tyr Tyr Gln Asp Glu Thr Thr Gly Arg Cys Glu Ala Cys Arg Val Cys
                115                 120                 125

Glu Ala Gly Ser Gly Leu Val Phe Ser Cys Gln Asp Lys Gln Asn Thr
    130                 135                 140

Val Cys Glu Glu Cys Pro Asp Gly Thr Tyr Ser Asp Glu Ala Asn His
145                 150                 155                 160

Val Asp Pro Cys Leu Pro Cys Thr Val Cys Glu Asp Thr Glu Arg Gln
                165                 170                 175

Leu Arg Glu Cys Thr Arg Trp Ala Asp Ala Glu Cys Glu Glu Ile Pro
                180                 185                 190

Gly Arg Trp Ile Thr Arg Ser Thr Pro Pro Glu Gly Ser Asp Ser Thr
                195                 200                 205

Ala Pro Ser Thr Gln Glu Pro Glu Ala Pro Pro Glu Gln Asp Leu Ile
    210                 215                 220

Ala Ser Thr Val Ala Gly Val Val Thr Thr Val Met Gly Ser Ser Gln
225                 230                 235                 240

Pro Val Val Thr Arg Gly Thr Thr Asp Asn Leu Ile Pro Val Tyr Cys
                245                 250                 255

Ser Ile Leu Ala Ala Val Val Val Gly Leu Val Ala Tyr Ile Ala Phe
                260                 265                 270

Lys Arg Trp Asn Ser Cys Lys Gln Asn Lys Gln Gly Ala Asn Ser Arg
                275                 280                 285

Pro Val Asn Gln Thr Pro Pro Glu Gly Glu Lys Leu His Ser Asp
    290                 295                 300

Ser Gly Ile Ser Val Asp Ser Gln Ser Leu His Asp Gln Gln Pro His
305                 310                 315                 320

Thr Gln Thr Ala Ser Gly Gln Ala Leu Lys Gly Asp Gly Gly Leu Tyr
                325                 330                 335

Ser Ser Leu Pro Pro Ala Lys Arg Glu Glu Val Glu Lys Leu Leu Asn
                340                 345                 350
```

```
Gly Ser Ala Gly Asp Thr Trp Arg His Leu Ala Gly Glu Leu Gly Tyr
        355                 360                 365

Gln Pro Glu His Ile Asp Ser Phe Thr His Glu Ala Cys Pro Val Arg
        370                 375                 380

Ala Leu Leu Ala Ser Trp Ala Thr Gln Asp Ser Ala Thr Leu Asp Ala
385                 390                 395                 400

Leu Leu Ala Ala Leu Arg Arg Ile Gln Arg Ala Asp Leu Val Glu Ser
                405                 410                 415

Leu Cys Ser Glu Ser Thr Ala Thr Ser Pro Val
                420                 425

(2) INFORMATION FOR SEQ ID NO:5:

(i) SEQUENCE CHARACTERISTICS:
        (A) LENGTH: 453 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:5:

Met Gly Leu Ser Thr Val Pro Asp Leu Leu Leu Pro Leu Val Leu Glu
1               5                   10                  15

Leu Leu Val Gly Ile Tyr Pro Ser Gly Val Ile Gly Leu Val Pro His
            20                  25                  30

Leu Gly Asp Arg Glu Lys Arg Asp Ser Val Cys Pro Gln Gly Lys Tyr
        35                  40                  45

Ile His Pro Asn Asn Ser Ile Cys Cys Thr Lys Cys His Lys Gly Thr
    50                  55                  60

Tyr Leu Tyr Asn Asp Cys Pro Gly Pro Gly Gln Asp Thr Asp Cys Arg
65                  70                  75                  80

Glu Cys Glu Ser Gly Ser Phe Thr Ala Ser Glu Asn His Leu Arg His
                85                  90                  95

Cys Leu Ser Cys Ser Lys Cys Arg Lys Glu Met Gly Gln Val Glu Ile
            100                 105                 110

Ser Ser Cys Thr Val Asp Arg Asp Thr Val Cys Gly Cys Arg Lys Asn
            115                 120                 125

Gln Tyr Arg His Tyr Trp Ser Glu Asn Leu Phe Gln Cys Phe Asn Cys
        130                 135                 140

Ser Leu Cys Leu Asn Gly Thr Val His Leu Ser Cys Gln Glu Lys Gln
145                 150                 155                 160

Asn Thr Val Cys Thr Cys His Ala Gly Phe Phe Leu Arg Glu Asn Glu
                165                 170                 175

Cys Val Ser Cys Ser Asn Cys Lys Lys Ser Leu Glu Cys Thr Lys Leu
            180                 185                 190

Cys Leu Pro Gln Ile Glu Asn Val Lys Gly Thr Glu Asp Ser Gly Thr
        195                 200                 205

Thr Val Leu Leu Pro Leu Val Ile Phe Phe Gly Leu Cys Leu Leu Ser
    210                 215                 220

Leu Leu Phe Ile Gly Leu Met Tyr Arg Tyr Gln Arg Trp Lys Ser Lys
225                 230                 235                 240

Leu Tyr Ser Ile Val Cys Gly Lys Ser Thr Pro Glu Lys Glu Gly Glu
                245                 250                 255

Leu Glu Gly Thr Thr Thr Lys Pro Leu Ala Pro Asn Pro Ser Phe Ser
            260                 265                 270
```

```
Pro Thr Pro Gly Phe Thr Pro Thr Leu Gly Phe Ser Pro Val Pro Ser
            275                 280                 285

Ser Thr Phe Thr Ser Ser Ser Thr Tyr Thr Pro Gly Asp Cys Pro Asn
    290                 295                 300

Phe Ala Ala Pro Arg Arg Glu Val Ala Pro Tyr Gln Gly Ala Asp
305             310                 315                 320

Pro Ile Leu Ala Thr Ala Leu Ala Ser Asp Pro Ile Pro Asn Pro Leu
                325                 330                 335

Gln Lys Trp Glu Asp Ser Ala His Lys Pro Gln Ser Leu Asp Thr Asp
            340                 345                 350

Asp Pro Ala Thr Leu Tyr Ala Val Glu Asn Val Pro Pro Leu Arg
    355                 360                 365

Trp Lys Glu Phe Val Arg Arg Leu Gly Leu Ser Asp His Glu Ile Asp
        370                 375                 380

Arg Leu Glu Leu Gln Asn Gly Arg Cys Leu Arg Glu Ala Gln Tyr Ser
385                 390                 395                 400

Met Leu Ala Thr Trp Arg Arg Arg Thr Pro Arg Arg Glu Ala Thr Leu
                405                 410                 415

Glu Leu Leu Gly Arg Val Leu Arg Asp Met Asp Leu Leu Gly Cys Leu
                420                 425                 430

Glu Asp Ile Glu Glu Ala Leu Cys Gly Pro Ala Ala Leu Pro Pro Ala
            435                 440                 445

Pro Ser Leu Leu Arg
        450

(2) INFORMATION FOR SEQ ID NO:6:

(i) SEQUENCE CHARACTERISTICS:
        (A) LENGTH: 467 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:6:

Met Ala Pro Pro Ala Arg Val His Leu Gly Ala Phe Leu Ala Val
1               5                   10                  15

Thr Pro Asn Pro Gly Ser Ala Ala Ser Gly Thr Glu Ala Ala Ala Ala
                20                  25                  30

Thr Pro Ser Lys Val Trp Gly Ser Ala Gly Arg Ile Glu Pro Arg
            35                  40                  45

Gly Gly Gly Arg Gly Ala Leu Pro Thr Ser Met Gly Gln His Gly Pro
50                  55                  60

Ser Ala Arg Ala Arg Ala Gly Arg Ala Pro Gly Pro Arg Pro Ala Arg
65                  70                  75                  80

Glu Ala Ser Pro Arg Leu Arg Val His Lys Thr Phe Lys Phe Val Val
                85                  90                  95

Val Gly Val Leu Leu Gln Val Val Pro Ser Ser Ala Ala Thr Ile Lys
                100                 105                 110

Leu His Asp Gln Ser Ile Gly Thr Gln Gln Trp Glu His Ser Pro Leu
            115                 120                 125

Gly Glu Leu Cys Pro Pro Gly Ser His Arg Ser Glu Arg Pro Gly Ala
            130                 135                 140

Cys Asn Arg Cys Thr Glu Gly Val Gly Tyr Thr Asn Ala Ser Asn Asn
145                 150                 155                 160
```

```
Leu Phe Ala Cys Leu Pro Cys Thr Ala Cys Lys Ser Asp Glu Glu Glu
            165                 170                 175

Arg Ser Pro Cys Thr Thr Thr Arg Asn Thr Ala Cys Gln Cys Lys Pro
            180                 185                 190

Gly Thr Phe Arg Asn Asp Asn Ser Ala Glu Met Cys Arg Lys Cys Ser
            195                 200                 205

Thr Gly Cys Pro Arg Gly Met Val Lys Val Lys Asp Cys Thr Pro Trp
            210                 215                 220

Ser Asp Ile Glu Cys Val His Lys Glu Ser Gly Asn Gly His Asn Ile
225                 230                 235                 240

Trp Val Ile Leu Val Val Thr Leu Val Val Pro Leu Leu Leu Val Ala
            245                 250                 255

Val Leu Ile Val Cys Cys Cys Ile Gly Ser Gly Cys Gly Gly Asp Pro
            260                 265                 270

Lys Cys Met Asp Arg Val Cys Phe Trp Arg Leu Gly Leu Leu Arg Gly
            275                 280                 285

Pro Gly Ala Glu Asp Asn Ala His Asn Glu Ile Leu Ser Asn Ala Asp
            290                 295                 300

Ser Leu Ser Thr Phe Val Ser Glu Gln Gln Met Glu Ser Gln Glu Pro
305                 310                 315                 320

Ala Asp Leu Thr Gly Val Val Gln Ser Pro Gly Glu Ala Gln Cys Leu
            325                 330                 335

Leu Gly Pro Ala Glu Ala Glu Gly Ser Gln Arg Arg Arg Leu Leu Val
            340                 345                 350

Pro Ala Asn Gly Ala Asp Pro Thr Glu Thr Leu Met Leu Phe Phe Asp
            355                 360                 365

Lys Phe Ala Asn Ile Val Pro Phe Asp Ser Trp Asp Gln Leu Met Arg
            370                 375                 380

Gln Leu Asp Leu Thr Lys Asn Glu Ile Asp Val Val Arg Ala Gly Thr
385                 390                 395                 400

Ala Gly Pro Gly Asp Ala Leu Tyr Ala Met Leu Met Lys Trp Val Asn
            405                 410                 415

Lys Thr Gly Arg Asn Ala Ser Ile His Thr Leu Leu Asp Ala Leu Glu
            420                 425                 430

Arg Met Glu Glu Arg His Ala Lys Glu Lys Ile Gln Asp Leu Leu Val
            435                 440                 445

Asp Ser Gly Lys Phe Ile Tyr Leu Glu Asp Gly Thr Gly Ser Ala Val
450                 455                 460

Ser Leu Glu
465

(2) INFORMATION FOR SEQ ID NO:7:

(i) SEQUENCE CHARACTERISTICS:
        (A) LENGTH: 343 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

GTCACGTTCC ATTATTTTAT TTAAAAACCT CAGTAATCGT TTTAGCTTCT TTCCAGCAAA      60

CTCTTCTCCA CAGTAGCCCA GTCGTGGTAG GATAAATTAC GGATATAGTC ATTCTAGGGG     120

TTTCAGTCTT TTCCATCTCA AGGCATTGTG TGTTTTGTTC CGGGACTGGT TTGGCTGGGA     180
```

```
CAAAGTTAGA ACTGCCTGAA GTTCGCACAT TCAGATTGTT GTGTCCATGG AGTTTTAGGA      240

GGGGATGGCC TTTCCGGTCT TCGCACTTCC ATCCTCTCCC ACTTCCATCT GGCGTCCACA      300

ACTTGTCCCC TGCACTTCTG GATGACACAG GGTGCTGCTG CCT                       343
```

(2) INFORMATION FOR SEQ ID NO:8:

(i) SEQUENCE CHARACTERISTICS:
        (A) LENGTH: 279 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

```
GTGGACGGTG CTTGGGAATG GTGTGAAATG GTTGCCGACT CAGGCATGGA TGGGCCCCTC       60

TCGCTTCTGG TGGTCTGTGA ACTGAGTCCC TGGGATGCCT TTAGGGCAGA GATTCCTGAG      120

CTGCGTTTTA GGGTACAGAT TCCCTGTTTG AGGAGCTTGG CCCCTCTGTA AGCGTCTGAC      180

TCATCTCAGA GATATCAATT CTTAAACACT GTGACAACGG GATCTAAAAT GGCTGACACA      240

TTTGTCCTTG TGTCACGTTC CATTATTTTA TTTAAAATT                             279
```

(2) INFORMATION FOR SEQ ID NO:9:

(i) SEQUENCE CHARACTERISTICS:
        (A) LENGTH: 250 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

```
GGCCACGTAG TGCCACGTGC CACAAACTAC GGGGGACGAT TTCTGATTGA ATTTTTGGCG       60

CTTTCAATCC ACCCTCCTCC CTTCTAATGG GACTTTGGGG ACAAAGGTCC GACCGCCTCG      120

AGCGTCGACA GGGCGCTATC CAGGAGCCAG GACAGCGTCG GGAACCAGAC CATGGCTCCT      180

GGACCCCAAG ATCCTTAAGT TCGTCGTCTT CATCGTCGGG TTCTCTGCCG GTAAGTTAGG      240

AGGTCCCTGG                                                             250
```

(2) INFORMATION FOR SEQ ID NO:10:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

```
CGCCCATGGC CACCATCCCC CGGCAG                                            26
```

(2) INFORMATION FOR SEQ ID NO:11:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

CGCAAGCTTT TAGTAGTGAT AGGGAGAGGC                                         30

(2) INFORMATION FOR SEQ ID NO:12:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

CGCGGATCCG CCATCATGGG ACTTTGGGGA CAA                                     33

(2) INFORMATION FOR SEQ ID NO:13:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

CGCGGTACCT TAGTAGTGAT AGGGAGAGGC                                         30

(2) INFORMATION FOR SEQ ID NO:14:

(i) SEQUENCE CHARACTERISTICS:
        (A) LENGTH: 58 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

CGCTCTAGAT CAAGCGTAGT CTGGGACGTC GTATGGGTAG TAAGTGATAG GGAGAGGC          58

(2) INFORMATION FOR SEQ ID NO:15:

(i) SEQUENCE CHARACTERISTICS:
        (A) LENGTH: 398 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:15:

GAGTTTGACC AGAGATGCAA GGGGTGAAGG AGCGCTTCCT ACCGTTAGGA ACTCTGGGGA         60

CAGAGCGCCC CGGCCGCCTG ATGGCGAGGC AGGGTGCGAC CCAGGACCCA GGACGGCGTC       120

GGGAACCATA CCATGGCCCG GATCCCCAAG ACCCTAAAGT TCGTCGTCGT CATCGTCGCG       180

GTCCTGCTGC CAGTCCTAGC TTACTCTGCC ACCACTGCCC GGCAGAGGGA AGTTCCCCAG       240

CAGACAGTGG CCCCACAGCA ACAGAGGCAC AGCTTCAAGG GGGAGGAGTG TCCAGCAGGA       300

TCTCATAGAT CAGAACATAC TGGAGCCTGT AACCCGTGCA CAGAGGGTGT GGATTACACC       360

AACGCTTCCA ACAATGAACC TTCTTGCTTC CCATGTAC                              398